US012698470B2

(12) United States Patent
Gadkari et al.

(10) Patent No.: US 12,698,470 B2
(45) Date of Patent: **\*Aug. 4, 2026**

(54) STABILITY OF MICROBIAL COMPOSITION, AND MANUFACTURING METHODS THEREFORE

(71) Applicant: Chr. Hansen A/S, Hoersholm (DK)

(72) Inventors: Pravin Gadkari, Andheri East (IN); Furqan Ali, Andheri East (IN); Surender Kumar Dhayal, Hoersholm (DK); Deepak Jain, Andheri East (IN)

(73) Assignee: Chr. Hansen A/S, Hoersholm (DK)

( \* ) Notice: Subject to any disclaimer, the term of this patent is extended or adjusted under 35 U.S.C. 154(b) by 159 days.

This patent is subject to a terminal disclaimer.

(21) Appl. No.: 18/713,292

(22) PCT Filed: Nov. 28, 2022

(86) PCT No.: PCT/EP2022/083455
§ 371 (c)(1),
(2) Date: May 24, 2024

(87) PCT Pub. No.: WO2023/094649
PCT Pub. Date: Jun. 1, 2023

(65) Prior Publication Data
US 2025/0019643 A1     Jan. 16, 2025

(30) Foreign Application Priority Data

Nov. 29, 2021    (IN) .............................. 202141055100

(51) Int. Cl.
*C12N 1/205*          (2026.01)
*C12N 11/04*          (2006.01)
*C12R 1/01*           (2006.01)
(52) U.S. Cl.
CPC .............. *C12N 1/205* (2021.05); *C12N 11/04* (2013.01); *C12R 2001/01* (2021.05)
(58) Field of Classification Search
CPC ...... C12N 1/205; C12N 11/04; C12R 2001/01
See application file for complete search history.

(56) References Cited

U.S. PATENT DOCUMENTS 4,436,813 A * 3/1984 Wood ................... C12N 11/089
435/182

FOREIGN PATENT DOCUMENTS

WO        2010138522 A2    12/2010
WO        2012077038 A1     6/2012

OTHER PUBLICATIONS

Dantas et al: "Current knowledge about physical properties of innovative probiotic spray-dried powders produced with lactose-free milk and prebiotics", LWT—Food Science and Technology, Academic Press, United Kingdom, vol. 151, Jul. 19, 2021 (Jul. 19, 2021).
Pinto et al: "A potential technological application of probiotic microcapsules in lactose-free Greek-style yoghurt", International Dairy Journal, Elsevier Applied Science, Barking, GB, vol. 97, Jun. 4, 2019 (Jun. 4, 2019), pp. 131-138.
Mishra et al: "Stress tolerance and physicochemical properties of encapsulation processes for Lactobacillus rhamnosus in pomegranate (*Punica granatum* L.) fruit juice", Food Science and Biotechnology, The Korea Soc. of Food Science and Technology, Heidelberg, vol. 25, No. 1, Feb. 29, 2016 (Feb. 29, 2016), pp. 125-129.
Verruck et al: "Effect of full-fat goat's milk and prebiotics use on Bifidobacterium BB-12 survival and on the physical properties of spray-dried powders under storage conditions", Food Research International, Elsevier, Amsterdam, NL, vol. 119, Oct. 12, 2018 (Oct. 12, 2018), pp. 643-652.
Seifert & Mogensen (2002), "Inventory of microoganisms with a documented history of use in food", (2002) Bulletin of the IDF No. 377, 10-19.
Zheng et al., "A taxonomic note on the genus *Lactobacillus*: Description of 23 novel genera, emended description of the genus *Lactobacillus* Beijerinck 1901, and union of Lactobacilloae and Leuconostocaceae", Int. J. Syst. Evol. Microbiol. 2020, 70, pp. 2782-2858.

* cited by examiner

*Primary Examiner* — Maryam Monshipouri
(74) *Attorney, Agent, or Firm* — Eric J. Fechter

(57) ABSTRACT
The present invention relates to encapsulation of microbial cultures to improve the robustness and stability upon storage. In particular, the present invention relates to dry preparations of microbial cultures, such as lactic acid bacteria (LAB), coated by a fat-matrix that increase survivability and mitigate post-acidification upon storage at ambient temperature for extended periods of time.

6 Claims, 13 Drawing Sheets

STABILITY OF MICROBIAL COMPOSITION, AND MANUFACTURING METHODS THEREFORE

CROSS-REFERENCE TO RELATED APPLICATIONS

This application is a 35 U.S.C. 371 national application of PCT/EP2022/083455, filed Nov. 28, 2022, which claims priority or the benefit from Indian Patent Application number 202141055100, filed Nov. 29, 2021. The contents of these applications are fully incorporated herein by reference.

FIELD OF THE INVENTION

The present invention relates to encapsulation of microbial cultures to improve the robustness and stability upon storage. In particular, the present invention relates to dry preparations of microbial cultures, such as lactic acid bacteria (LAB), coated by a fat-matrix that increase survivability and mitigate post-acidification upon storage at ambient temperature for extended periods of time.

BACKGROUND OF THE INVENTION

It is a common practice to produce dry microorganism for extended application and storage by either freeze drying or spray drying. These dried microorganisms are intended to be used in industrial and food applications such as making yoghurt, cheese and as probiotics. Dried microorganisms are produced in highly concentrated form and then added to food and, feed matrices or diluted in excipient. It is also evident that dried microorganisms degrade to some extended upon storage at ambient temperature, specially cell viability, thereby losses functional activity. Further, it is also well established that combination of increased temperature and high humid environment significantly increase the loss of viability of dried microorganism upon storage. Various approaches such as addition of cryoprotectant before the drying of microorganism and fat coating after drying have been tried in literature to overcome stresses of ambient humid environment to the dried microorganisms, but with only limited success. Thus, producing shelf stable dried microorganism in ambient humid environment remains unmet objective.

The LAB are produced using fermentation process followed by cell concentration step to obtain cell biomass. Cryoprotectants are added to cell biomass before drying in order to increase the process and storage stability.

Stable dry powder compositions comprising biologically active microorganisms are known in the art, such as through WO2010138522A2. However, there is still a need for improved processes and formulations suitable for microorganisms.

SUMMARY OF THE INVENTION

The present invention seeks to overcome disadvantages in existing solutions by providing improvements specifically suited for micro-encapsulation of live microogranisms, such as probiotics.

The invention relates generally to improving the protective compound(s) added to microbial cultures before encapsulation. In particular, the present invention discloses methods for preparing dry microbial cultures with a cryoprotectant and/or lyoprotectant, which allows the microbial culture to maintain viability during a post-pasteurization step and throughout subsequent storage at ambient temperature. The encapsulated microbial cultures constitute an improved biocompatible option for applications wherein the microbial culture must be added prior to a pasteurization step.

Accordingly, an object of the present invention relates to the provision of a composition providing enhanced stability for microbial cultures.

According to a first aspect, a method for the preparation of a composition comprising a microencapsulated microbial culture is provided. The method comprises the steps of; obtaining a concentrated cell mass of the microbial culture; adding a protective compound to the concentrated cell mass to obtain a mixture; drying the mixture to obtain dried mixture; optionally grinding the dried mixture to obtain powder; coating the powder; and optionally mixing the coated powder with an excipient; wherein the wherein the protective compound is a cryoprotectant and/or lyoprotectant with a bulk density between 150 and 600 kg/m$^3$.

In an embodiment, the protective compound is a cryoprotectant and/or lyoprotectant with a bulk density between 150 and 225 kg/m$^3$.

In an embodiment, the protective compound is a cryoprotectant and/or lyoprotectant with a bulk density of about 180 kg/m$^3$.

In an embodiment, the coating is a fat coating.

In an embodiment, the method further comprises the step of adjusting the water activity ($a_w$) of the mixture of pellet and excipient to about 0.35.

In one embodiment, the protective compound is a cryoprotectant and/or lyoprotectant comprising at least one ingredient selected form the list consisting of maltodextrin, oligofructose, pectin, xanthan gum, OSA starch and sodium ascorbate.

In one embodiment, the excipient is calcium carbonate.

In one embodiment, the drying is conducted by a method selected from the group consisting of desiccation, fluidized bed drying, freeze-drying, vacuum-drying, and spray-drying.

According to a second aspect, a composition comprising a microencapsulated microbial culture prepared by the method according to the first aspect is provided, wherein said composition is stable at ambient temperature for at least 12 weeks with a $\log_{10}$ loss of less than 4 cfu/g.

According to a third aspect, a composition comprising a microencapsulated microbial culture is provided, comprising powder comprising a protective compound and a coating, wherein the protective compound is a cryoprotectant and/or lyoprotectant with a bulk density between 150 and 600 kg/m$^3$ In one embodiment, the protective compound is a cryoprotectant and/or lyoprotectant with a bulk density between 150 and 225 kg/m$^3$.

In one embodiment, the protective compound is a cryoprotectant and/or lyoprotectant with a bulk density of about 180 kg/m$^3$.

In one embodiment, the composition further comprises an excipient.

In one embodiment, the excipient is calcium carbonate.

In one embodiment, the coating is a fat coating.

In one embodiment, the fat is selected from the group consisting of hydrogenated vegetable oil, hydrogenated palm fatty acid derivate, glyceride of saturated fatty acid and glyceride, palm stearin, bees wax, carnauba wax, candelilla wax, emulsifying wax and soy wax.

In one embodiment, the fat is a blend of a first fat and a second fat, wherein the first fat is hydrogenated vegetable oil and the second fat is selected from the group comprising palm stearin, bees wax, carnauba wax, candelilla wax, emulsifying wax and soy wax; or wherein the first fat is hydrogenated palm fatty acid derivate and the second fat is selected from the group comprising palm stearin, bees wax, carnauba wax, candelilla wax, emulsifying wax and soy wax; or wherein the first fat is glyceride of saturated fatty acid and the second fat is selected from the group comprising palm stearin, bees wax, carnauba wax, candelilla wax, emulsifying wax and soy wax; or wherein the first fat is glyceride and the second fat is selected from the group comprising palm stearin, bees wax, carnauba wax, candelilla wax, emulsifying wax and soy wax.

In one embodiment, the microbial culture is selected from one or more of *Lactobacillus, Holzapfelia, Amylolactoba- cillus, Bombilactobacillus, Companilactobacillus, Lapidi- lactobacillus, Agrilactobacillus, Schleiferilactobacillus, Loigolactobacilus, Lacticaseibacillus, Latilactobacillus, Dellaglioa, Liquorilactobacillus, Ligilactobacillus, Lacti- plantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus, Leuconostoc, Pediococcus, Lacto- coccus, Streptococcus, Enterococcus, Propionibacterium, Bifidobacterium, Brevibacterium, Saccharomyces* and *Staphylococcus.*

In a preferred embodiment, the microbial culture is selected from the group consisting of *Ligilactobacillus ani- malis* (DSM 33570), *Bifidobacterium animalis* subsp. *Lactis* (DSM 15954), *Lactobacillus acidophilus* (DSM 13241), *Streptococcus thermophilus* (DSM 15957) and *Lactococcus lactis* subsp. *Lactis* (DSM 21404).

In a particularly preferred embodiment, the microbial culture is *Ligilactobacillus animalis* (DSM 33570).

DEFINITIONS

Prior to outlining the present invention in more details, a set of terms and conventions is first defined:

Microbial Culture

In the present context, the term "microbial culture" refers to a population of microorganisms. Microorganisms include all unicellular organisms, such as archaea and bacteria, but also many multicellular organisms, such as fungi and algae.

Probiotic Culture

In the present context, the terms "probiotic" or "probiotic culture" refers to microbial cultures which, when ingested in the form of viable cells by humans or animals, confer an improved health condition, e.g. by suppressing harmful microorganisms in the gastrointestinal tract, by enhancing the immune system or by contributing to the digestion of nutrients. Probiotics may also be administered to plants. Probiotic cultures may comprise bacteria and/or fungi.

Lactic Acid Bacteria (LAB)

In the present context, the term "lactic acid bacteria (LAB)" refers to a group of Gram positive, catalase nega- tive, non-motile, microaerophilic or anaerobic bacteria that ferment sugar with the production of acids including lactic acid as the predominantly produced acid, acetic acid, formic acid and propionic acid. The industrially most useful lactic acid bacteria include, but are not limited to, *Lactococcus* species (spp.), *Streptococcus* spp., *Lactobacillus* spp., *Leu- conostoc* spp., *Pediococcus* spp., *Brevibacterium* spp, *Enterococcus* spp. and *Propionibacterium* spp. Additionally, lactic acid producing bacteria belonging to the group of the strict anaerobic bacteria, Bifidobacteria, i.e. *Bifidobacterium* spp. which are frequently used as food starter cultures alone or in combination with lactic acid bacteria, are generally included in the group of lactic acid bacteria. Even certain bacteria of the genus *Staphylococcus* (e.g. *S. carnosus, S. equorum, S. sciuri, S. vitulinus* and *S. xylosus*) have been referred to as LAB (Seifert & Mogensen (2002)).

Viability

In the present context, the term "viability" refers to living cells in a culture. Thus, the viability of a cell culture may be determined by measuring the number of colony forming units (CFU). CFU refer to the number of individual colonies of any microbe that grow on a plate of media. This value in turn represents the number of bacteria or fungi capable of replicating as they have formed colonies on the plate.

In brief, the CFU/g can be determined as follows; A known amount of sample (e.g. freeze dried) is homogenized with a specific volume of diluent (1:100), using a stomacher, the solution is then resuspended by using a vortex mixer and is then subjected to decimal dilutions in peptone saline diluent (also referred to as 'maximum recovery diluent (MRD)'). MRD comprises peptone, NaCl and demineralised water. Dilutions are poured on the plates, mixed with MRS Agar (Hi-media, M641) and incubated. After incubation, colonies are counted manually.

Particularly, stability of a sample is assessed by counting the colony-forming units (CFU) per gram, using the follow- ing assay. Viable cell counts are determined in freeze-dried granulates sampled immediately after freeze-drying and at selected time points during the stability studies. A standard pour-plating method is used. The freeze-dried material is suspended in sterile peptone saline diluent (BD Difco™ Lactobacilli MRS Agar, Fisher Scientific) and homogenized by stomaching using stomacher (bioMerieux, Inc. Durham, NC). After 30 minutes of revitalization, stomaching is repeated and the cell suspension is serially diluted in pep- tone saline diluent. For the cfu of *Bifidobacterium animalis* subsp. *lactis* deposited as DSM 15954 (BB-12®), the dilu- tions are plated in duplicates on MRS agar (BD Difco™ Lactobacilli MRS Agar, Fisher Scientific) supplemented with 0.5 g/L of L-cysteine hydrochloride (Sigma-Aldrich, Inc.). The agar plates are incubated anaerobically for three days at 37° C. For the cfu of *Ligilactobacillus animalis* LA51, deposited as DSM 33570, the dilutions are plated in duplicates on MRS agar (BD Difco™ Lactobacilli MRS Agar, Fisher Scientific). The agar plates are incubated anaerobically for three days at 37° C. In case of *Strepto- coccus thermophilus* TH4 (DSM 15957) cfu, the dilutions are plated in duplicates on M17 agar (BD Difco™ Lacto- bacilli MRS Agar, Fisher Scientific) supplemented with 0.5 g/L of monosodium phosphate (Sigma-Aldrich, Inc.) and 0.5 g/L of disodium phosphate (Sigma-Aldrich, Inc.). The agar plates are incubated aerobically for three days at 37° C. For the cfu of *Lactococcus lactis* subsp. *lactis* R607 (DSM 21404), the dilutions are plated in duplicates on M17 agar (BD Difco™ Lactobacilli MRS Agar, Fisher Scientific) supplemented with 0.5 g/L of monosodium phosphate (Sigma-Aldrich, Inc.) and 0.5 g/L of disodium phosphate (Sigma-Aldrich, Inc.). The agar plates are incubated aero- bically for three days at 37° C. Plates with 30-300 colonies are chosen for counting of colony forming units (CFU). The result is reported as average CFU/g freeze-dried sample, calculated from the duplicates.

Microencapsulated

In the present context, the term "microencapsulated" refers to an entity, which on a micrometric scale are secluded from the surrounding environment. Thus, a microencapsu- lated microbial culture is a microbial culture which are compartmentalized into distinct entities separated from each other and the medium into which they are dispersed.

Powder

In the present context, the term "powder" refers to ground particles with an average particle size between 40 and 250 μm, preferably between 100 and 250 μm.

Complex Coacervate

In the present context, the term "complex coacervate" refers to an aqueous phase (or droplet) rich in the microbial culture that is formed upon complex coacervation using two or more biopolymers of opposite charge. The complex coacervate forms due to liquid-liquid phase separation and is a dense phase that exist in equilibrium with a dilute phase. Thus, the complex coacervate may be characterized as a lyophilic colloid.

The method of complex coacervation involves the mixing of an entity to be encapsulated, such as a microbial culture, with at least two biopolymers of opposite charge. Herein, the biopolymers of opposite charge are referred to as coacervate components and comprised in a first and second matrix, respectively.

Antioxidant

In the present context, the term "antioxidant" refers to a compound that inhibit oxidation. The antioxidant may be industrial chemicals or natural compounds. As used herein, antioxidants include, but are not limited to, trisodium citrate, vitamin C, vitamin E, glutathione and derivatives thereof.

It is to be understood that antioxidants as used herein include mineral salts of vitamin C, such as sodium ascorbate. Also, the vitamin E is to be understood as including all variants of tocopherols and tocotrienols (alpha, beta, gamma, delta).

Hydrophobic Coating

In the present context, the term "hydrophobic coating" refers to a hydrophobic layer or shell that is positioned on the surface of the complex coacervate. Such hydrophobic layer or shell may comprise one or more hydrophobic compounds or molecules comprising a hydrophobic moiety that cause the outer surface of the complex coacervate to be hydrophobic.

Food-Grade Ingredient

In the present context, the term "food-grade ingredient" refers to any compound that is non-toxic and safe for consumption and comply with the Food Chemicals Codex (FCC). Food-grade ingredients include, but are not limited to, compounds that can alter attributes such as aroma, flavour, acidity, colour, viscosity and texture, as well as preservatives, nutrients, thickeners, sweeteners and emulsifiers.

Preferred food-grade ingredients include, but are not limited to, lactose, maltodextrin, whey protein, casein, corn starch, dietary fibres, gums and gelatine.

Pharmaceutical Ingredient

In the present context, the term "pharmaceutical ingredient" refers to an ingredient in a pharmaceutical formulation that is not an active ingredient.

Pharmaceutical ingredients include, but are not limited to, calcium carbonate, sodium carboxymethyl cellulose, talc, polydimethylsiloxane, hydroxypropyl cellulose and hydroxypropyl methylcellulose.

Excipient

In the present context, the term "excipient" refers to a natural or synthetic substance formulated alongside the active ingredient or pharmaceutical ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing solubility, adjusting tonicity, mitigating injection site discomfort, depressing the freezing point, or enhancing stability.

Excipients include, but are not limited to, microcrystalline cellulose, titanium dioxide and aluminium silicate.

Storage Stability

In the present context, the term "storage stability" refers to the ability of a microencapsulated microbial culture to maintain viability when stored at accelerated storage conditions over an extended duration of time, such as at a temperature of 25° C. and a water activity $(A_w) \leq 0.35$ for a period of 12 weeks. $A_w$ of a food is the ratio between the vapor pressure of the microencapsulated microbial culture itself, when in a completely undisturbed balance with the surrounding air media, and the vapor pressure of distilled water under identical conditions. In the present context $A_w$ is measured either by a resistive electrolytic, a capacitance or a dew point hygrometer.

Storage stability can be determined by analysing how the count of viable microbial cells develop over time. Viability of the microbial culture is measured by determining the CFU/g as described herein. Thus, a measure of the storage stability of the microencapsulated microbial culture may be determined by evaluating CFU/g of the dry powder of microencapsulated microbial culture at time point 0, 2, 4, 8 and 12 weeks of storage at accelerated storage conditions.

DETAILED DESCRIPTION OF THE INVENTION

Figure 1A:
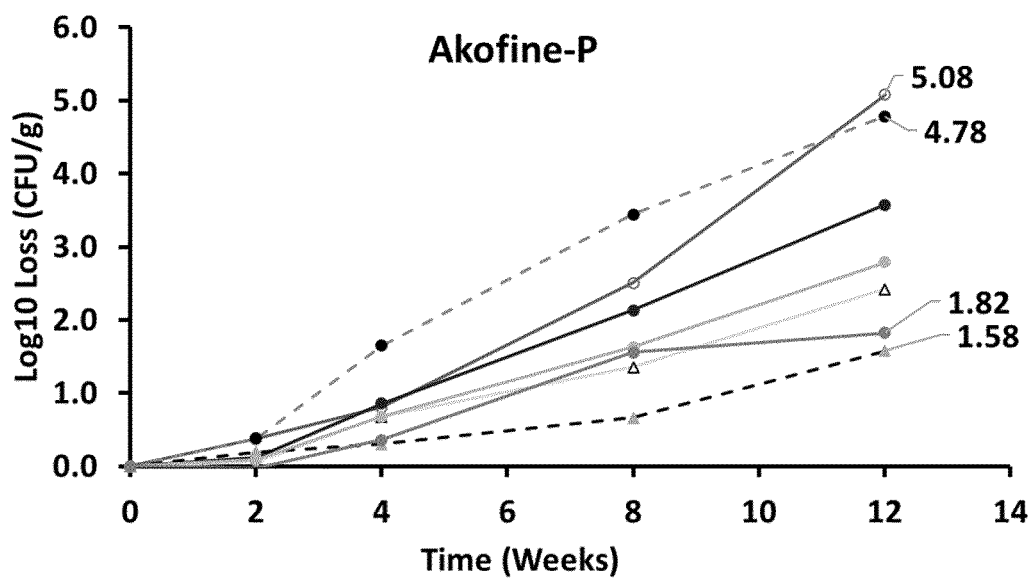
FIG. 1A-1D show the stability curve of fat coated cryoprotectant powder using different fat blend mixtures according to various embodiments.
Figure 1B:
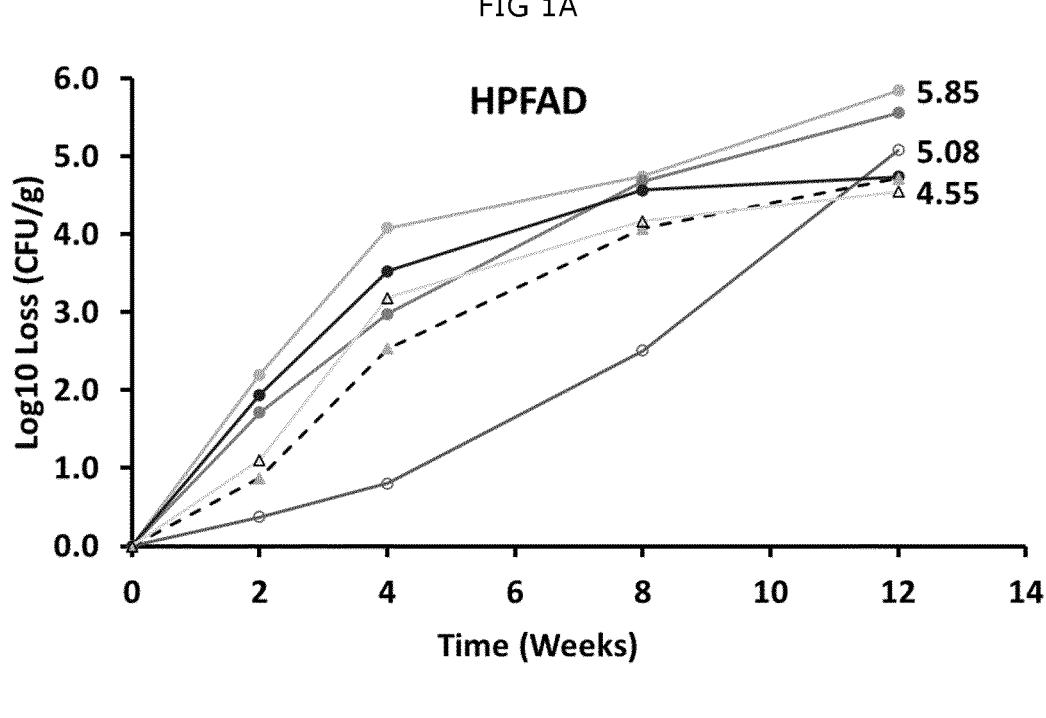

Microbial cultures, such as lactic acid bacteria (LAB), play key parts in many fermented products, in which they add nutritional value to the product and improve the organoleptic and textural profile of e.g. food products. The microbial cultures are typically acquired separately as powdered compositions and mixed with additional ingredients to yield a final product. Thus, the powdered composition comprising the microbial culture need as a minimum to maintain viability from the point of becoming a dried granulate to the point at which the powdered microbial cultures is included in a final product. Ideally, the microbial cultures are kept refrigerated during transport, supplementary processing and as part of the final product. However, this is not always possible as cold transport and storage is both expensive and, in many cases, not feasible in e.g. developing countries or remote regions. Moreover, the final product may be an article that is not readily stored under refrigerated conditions. This is typically the case of animal feed.

To deliver microbial cultures of high quality, e.g. high viability, under such environmental stress conditions, it is a necessary to decrease yield loss during downstream processing and eliminate the requirement of refrigerated transport and storage. However, no methods exist that both provide adequate cryo/lyo protection and enhance storage stability at elevated temperatures.

Herein are set out methods for encapsulating microbial cultures in a matrix comprising one or more fat components. Without being bound theory, the encapsulation matrix assists in absorbing heat from the environment and protect the cells during the time scale of heating. Moreover, it was found that the fat encapsulation efficiently mitigates any significant post-acidification of the microbial culture upon storage at ambient conditions for extended periods of time.

Two types of microorganisms that are of great importance in many consumer goods are bacteria and yeast. These microorganisms are included e.g. in fermented food, feed mixes and nutritional supplements, wherein their health benefits are well-documented.

Therefore, an embodiment of the present invention relates to the microencapsulated microbial culture as described herein, wherein the microbial culture is a bacterium or a yeast.

Another embodiment of the present invention relates to the microencapsulated microbial culture as described herein, wherein the microbial culture is or comprises a genus selected from the group consisting of *Lactobacillus, Leuconostoc, Pediococcus, Lactococcus, Streptococcus, Entero-*

*coccus, Bifidobacterium, Propionibacterium, Brevibacterium, Staphylococcus, Bacillus* and *Saccharomyces.*

Of particular interest are lactic acid bacteria (LAB) that are an order of Gram-positive bacteria sharing common metabolic and physiological characteristics. LAB produce lactic acid as the major metabolic outcome of carbohydrate fermentation. Ever since it was discovered that acidification by food fermentation could preserve food by inhibiting growth of spoilage agents, LAB has been utilized purposefully in food fermentation. However, since efficient food fermentation requires high quality viable microorganisms, the development of fermented foods has been halted in areas that do not have advanced facilities to handle the fragile microorganisms.

Specifically, microbial cultures, such as LAB, are not easily handled in some developing countries or remote regions due to the requirement and cost of refrigerated facilities. The microencapsulated microbial cultures described herein tolerate storage at elevated temperatures and may thus open up development of products containing microbial cultures, such as LAB, to a broader ensemble of product developers.

Thus, an embodiment of the present invention relates to the microencapsulated microbial culture as described herein, wherein the microbial culture is a lactic acid bacteria (LAB). Another embodiment of the present invention relates to the microencapsulated microbial culture as described herein, wherein the microbial culture is or comprises a lactic acid bacteria (LAB) of a genus selected from the group consisting of *Lactobacillus, Holzapfelia, Amylolactobacillus, Bombilactobacillus, Companilactobacillus, Lapidilactobacillus, Agrilactobacillus, Schleiferilactobacillus, Loigolactobacillus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus, Leuconostoc, Pediococcus, Lactococcus, Streptococcus, Enterococcus, Bifidobacterium, Brevibacterium,* and *Staphylococcus.*

Thus, an embodiment of the present invention relates to the microencapsulated microbial culture as described herein, wherein the microbial culture is or comprises a lactic acid bacteria (LAB) of a genus selected from the group consisting of *Lactobacillus, Limosilactobacillus, Lacticaseibacillus, Ligilactobacillus, Lacticaseibacillus, Lacticaseibacillus, Lactiplantibacillus, Limosilactobacillus, Ligilactobacillus, Lentilactobacillus, Latilactobacillus, Companilactobacillus, Latilactobacillus* and *Lactiplantibacillus.* Another embodiment of the present invention relates to the microencapsulated microbial culture as described herein, wherein the microbial culture is of a species of *Limosilactobacillus reuteri, Lacticaseibacillus rhamnosus, Ligilactobacillus salivarius, Lacticaseibacillus casei, Lacticaseibacillus paracasei* subsp. *paracasei, Lactiplantibacillus plantarum* subsp. *plantarum, Limosilactobacillus fermentum, Ligilactobacillus animalis, Lentilactobacillus buchneri, Latilactobacillus curvatus, Companilactobacillus futsaii, Latilactobacillus sakei* subsp., *Lactiplantibacillus pentosus, Lactobacillus acidophillus, Lactobacillus helveticus, Lactobacillus gasseri* and *Lactobacillus delbrueckii.*

DEPOSIT AND EXPERT SOLUTION

The applicant requests that a sample of the deposited microorganisms stated below may only be made available to an expert, subject to available provisions governed by Industrial Property Offices of States Party to the Budapest Treaty, until the date on which the patent is granted.

TABLE 1

Deposits made at a Depositary institution having acquired the status of international depositary authority under the Budapest Treaty on the International Recognition of the Deposit of Microorganisms for the Purposes of Patent Procedure: Leibniz Institute DSMZ-German Collection of Microorganisms and Cell Cultures Inhoffenstr. 7B, 38124 Braunschweig, Germany.

| Strain | Accession No. | Deposit date |
|---|---|---|
| *Ligilactobacillus animalis* (LA51) | DSM 33570 | 8 Jul. 2020 |
| *Bifidobacterium animalis* subsp. *lactis* | DSM 15954 | 30 Sep. 2003 |
| *Lactobacillus acidophilus* | DSM 13241 | 20 Jan. 2000 |
| *Streptococcus thermophilus* | DSM 15957 | 30 Sep. 2003 |
| *Lactococcus lactis* subsp. *Lactis* | DSM 21404 | 23 Apr. 2008 |

Taxonomy

It will be appreciated that the *Lactobacillus* genus taxonomy was updated in 2020. The new taxonomy is disclosed in Zheng et al. 2020 and will be cohered to herein if nothing else is noticed. For the purpose of the present invention, Table 2. New and old names of some *Lactobacillus* species relevant to the present invention, presents a list of new and old names of some *Lactobacillus* species relevant to the present invention.

TABLE 2

New and old names of some *Lactobacillus* species relevant to the present invention.

| Old Name | New Name |
|---|---|
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |
| *Lactobacillus casei* | *Lacticaseibacillus casei* |
| *Lactobacillus paracasei* subsp. *paracasei* | *Lacticaseibacillus paracasei* subsp. *Paracasei* |
| *Lactobacillus plantarum* subsp. *plantarum* | *Lactiplantibacillus plantarum* subsp. *Plantarum* |
| *Lactobacillus fermentum* | *Limosilactobacillus fermentum* |
| *Lactobacillus animalis* | *Ligilactobacillus animalis* |
| *Lactobacillus buchneri* | *Lentilactobacillus buchneri* |
| *Lactobacillus curvatus* | *Latilactobacillus curvatus* |
| *Lactobacillus futsaii* | *Companilactobacillus futsaii* |
| *Lactobacillus sakei* subsp. *sakei* | *Latilactobacillus sakei* subsp. |
| *Lactobacillus pentosus* | *Lactiplantibacillus pentosus* |

EXAMPLES

Example 1: Fat and Wax Coatings

This example demonstrate the use of different fat blends with defined melting point and crystallization properties and their compatibility with cryoprotectant, as well as their ability to improve the storage stability of LAB at ambient humid conditions (T=25° C. and $a_w$=0.35). It is shown that certain coating compositions provide better protection to LAB compared to non-coated cryoprotectant after 12 weeks of ambient humid storage.

Fresh *Lactobacillus animalis* (LA51) cell concentrate was produced according to methods well known to a person skilled in the art. The cell concentrate is mixed with a cryoprotectant (CP) formulation according to the specification of Table 3.

TABLE 3

The composition of cryoprotectant (%, w/w) used for fat coating.

| Sr. No. | Ingredients | CP (w/w, %) |
|---|---|---|
| 1 | Maltodextrin DE12 | 5.00 |
| 2 | Trehalose | 23.00 |
| 3 | Tri-sodium Citrate | 5.00 |
| 4 | RO water | 67.00 |

Cryoprotectant (CP) was prepared in ratio as mentioned in Table 3. Maltodextrin, Trehalose and water were mixed and then autoclaved. Trisodium citrate solution (30%, w/w) was prepared and then added to the CP. The freshly produced LA51 biomass was mixed with CP for 2 h at 10° C. followed by pelletization in liquid nitrogen, forming powder. These pre-freeze dried (PFD) powder were freeze dried using at 32° C., 0.3 mbar for 26 h, by loading the PFDs into a labelled pre-frozen metal container and drying them in using a Martin Christ freeze dryer (Germany, GmbH). The freeze dried (FD) powder or granulates were ground and sieved to get a fine ground FD-cryo powder with particle size close to 60 mesh (250 μm). The cryoprotectant powder was blended with an excipient calcium carbonate ($CaCO_3$) having the water activity ($a_w$) of 0.35. The blend was prepared by mixing 1 part of finely ground CP powder with 24 parts of $CaCO_3$ ($a_w$=0.35). The blends of CP powder with $CaCO_3$ was subjected to stability chamber maintained at 25° C. to check their storage stability. The $a_w$ of the final blend (cryoprotectant powder and $CaCO_3$) was determined to ensure $a_w$=0.35. The samples were withdrawn at predetermined time intervals and analyzed for CFU/g to give the viability of microbial cultures under storage.

In the next set, the FD cryoprotectant powders were coated with a fat using the following fat palletization process. Fat mixture (FAT-A and Wax-B), as shown in Table 4, was molten by heating the contents to a temperature between 70° C. to 85° C. for 15 min. Melting points of fat and waxes used in fat blends for coating are summarized in Table 4.

The CP powder was dispersed into the molten fat blends and homogenized for 5 min using rotor stator homogenizer. The homogenized molten mixture was dripped on a stainless steel (SS) sheet, which was maintained at 23° C. for 1 min which allowed the molten fat to solidify. Finally, the fat powder were recovered from the stainless steel sheet and stored in a refrigerator (4-10° C.) until its further use.

TABLE 4

Fat mixture used for fat coating of cryoprotectant powders.

| No. | Product code | FAT-A | FAT-A (g) | Wax-B | Wax-B (g) | CP (g) | Total (g) |
|---|---|---|---|---|---|---|---|
| 1 | FB-01 | Akofine P ™ | 64 | Palm stearin | 16 | 20 | 100 |
| 2 | FB-02 | Akofine P ™ | 64 | Bees wax | 16 | 20 | 100 |
| 3 | FB-03 | Akofine P ™ | 64 | Carnauba wax | 16 | 20 | 100 |
| 4 | FB-04 | Akofine P ™ | 64 | Candelilla wax | 16 | 20 | 100 |
| 5 | FB-05 | Akofine P ™ | 64 | Emulsifying wax | 16 | 20 | 100 |
| 6 | FB-06 | Akofine P ™ | 64 | Soy wax | 16 | 20 | 100 |

TABLE 4-continued

Fat mixture used for fat coating of cryoprotectant powders.

| No. | Product code | FAT-A | FAT-A (g) | Wax-B | Wax-B (g) | CP (g) | Total (g) |
|---|---|---|---|---|---|---|---|
| 7 | FB-07 | HPFAD | 64 | Emulsifying wax | 16 | 20 | 100 |
| 8 | FB-08 | HPFAD | 64 | Soy wax | 16 | 20 | 100 |
| 9 | FB-09 | HPFAD | 64 | Bees wax | 16 | 20 | 100 |
| 10 | FB-10 | HPFAD | 64 | Candelilla wax | 16 | 20 | 100 |
| 11 | FB-11 | HPFAD | 64 | Carnauba wax | 16 | 20 | 100 |
| 12 | FB-12 | Dynasan ® P60 | 64 | Bees wax | 16 | 20 | 100 |
| 13 | FB-13 | Dynasan ® P60 | 64 | Emulsifying wax | 16 | 20 | 100 |
| 14 | FB-14 | Dynasan ® P60 | 64 | Candelilla wax | 16 | 20 | 100 |
| 15 | FB-15 | Dynasan ® P60 | 64 | Soy wax | 16 | 20 | 100 |
| 16 | FB-16 | Dynasan ® P60 | 64 | Carnauba wax | 16 | 20 | 100 |
| 17 | FB-17 | Softisan ® 100 | 64 | Emulsifying wax | 16 | 20 | 100 |
| 18 | FB-18 | Softisan ® 100 | 64 | Soy wax | 16 | 20 | 100 |
| 19 | FB-19 | Softisan ® 100 | 64 | Bees wax | 16 | 20 | 100 |
| 20 | FB-20 | Softisan ® 100 | 64 | Carnauba wax | 16 | 20 | 100 |
| 21 | FB-21 | Softisan ® 100 | 64 | Candelilla wax | 16 | 20 | 100 |

The fat powder prepared using different fat blends as shown in Table 4 were then blended into $CaCO_3$ with $a_w=0.35$ (1 g of fat powder:24 g of $CaCO_3$). In this process, the mixture of fat powder and $CaCO_3$ were ground to achieve a uniform size (60 mesh, 250 µm) of both fat powder and $CaCO_3$. The mixture of fat powder and $CaCO_3$ was packed into Alu-pouches and stored at 25° C. in a stability chamber (T=25° C. and $a_w=0.35$). The samples were withdrawn at predetermined time intervals and analyzed for viability (CFU/g). For conducting the CFU analysis, the fat coated samples were allowed to decapsulate using decapsulation buffer (Maximum Recovery Diluent supplemented with 1.0% Tween 80). The $CaCO_3$ blended fat coated sample was weighed and transferred to stomacher bag containing decapsulation buffer. This mixture was allowed to stomach using stomacher at normal speed for 2 min. Then the stomacher bag containing sample was incubated at 37° C. for 30 min in incubator. After incubation, the stomacher bag was again allowed to stomach at normal speed for 2 min. Sample from stomacher bag was taken for CFU analysis using serial dilution method.

TABLE 5

Melting points of fat and waxes used in fat blends for coating.

| Sr. No. | Fats/Waxes with Trade name | Chemical/Common name | CAS number | Melting point (° C.) |
|---|---|---|---|---|
| 1 | Akofine P ™ | Hydrogenated Vegetable oil | 68334-28-1 | 60 |
| 2 | HPFAD (Hydrogenated palm fatty acid derivatives) | Hydrogenated palm fatty acid derivatives | NA | 54 |
| 3 | Dynasan ® P60 | Glycerides of Saturated fatty acids | NA | 58 |

TABLE 5-continued

Melting points of fat and waxes used in fat blends for coating.

| Sr. No. | Fats/Waxes with Trade name | Chemical/Common name | CAS number | Melting point (° C.) |
|---|---|---|---|---|
| 4 | Softisan ® 100 | Glycerides, C12-18 | 67701-26-2 | 36 |
| 5 | Palm sterin | Palm kernel stearin | 91079-14-0 | 56 |
| 6 | Bees wax | Bees wax | 8012-89-3 | 65 |
| 7 | Carnauba wax | Carnauba wax | 8015-86-9 | 86 |
| 8 | Candellila wax | Candellila wax | 8006-44-8 | 77 |
| 9 | Emulsifying wax | Emulsifying wax | 8014-38-8 | 54 |
| 10 | Soy wax | Soy wax | 8016-74-0 | 67 |

FIG. 1 shows the stability curve of fat coated CP powder using different fat blend mixtures stored at $a_w=0.35$ and T=25° C. FIG. 1A is a graph showing stability data where Akofine P™ is Fat A. FIG. 1B is a graph showing stability data where HPFAD is Fat A. FIG. 1C is a graph showing stability data where Akofine P™ is Fat A. FIG. 1A is a graph showing stability data where Akofine P™ is Fat A.

The FD granulate of CP containing LA51 was ground to get a fine powder (≤250 micron) and it was blended 25 times with the $CaCO_3$ having water activity of 0.35 and stored at ambient temperature (25° C.) (Table 3). It was seen from FIG. 1 that the non-coated (control) CP had poor storage stability compared to all other fat blend coated CP. This could be due to the presence of uniform layer of hydrophobic fat over the CP powder which further restricted the moisture migration from excipient and enhanced the storage stability.

Figure 1C:
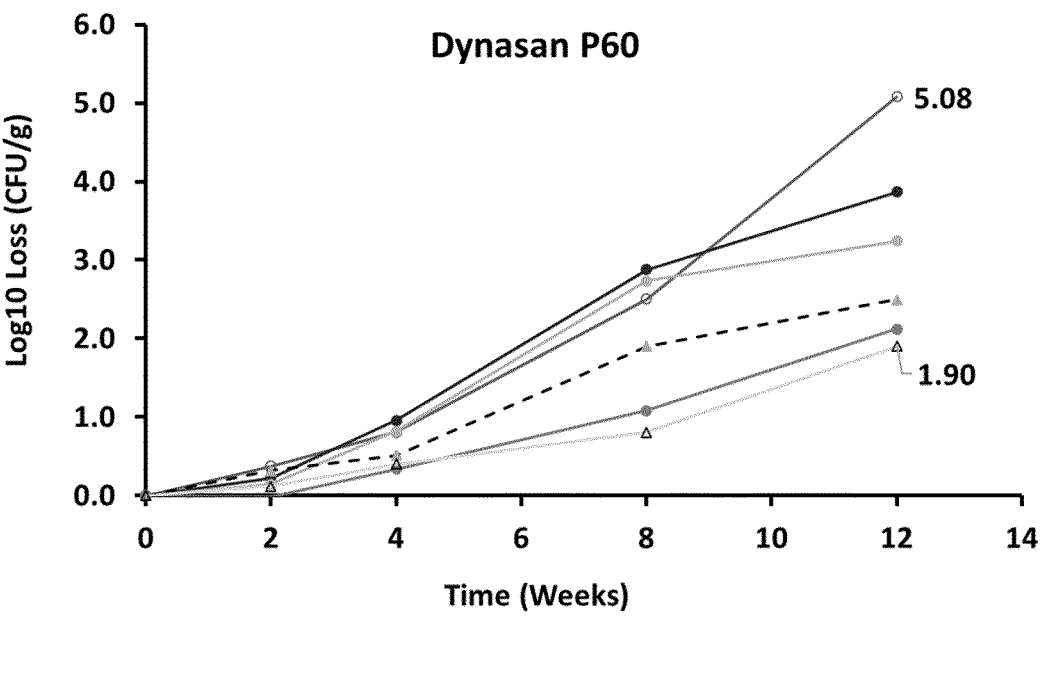
Figure 1D:
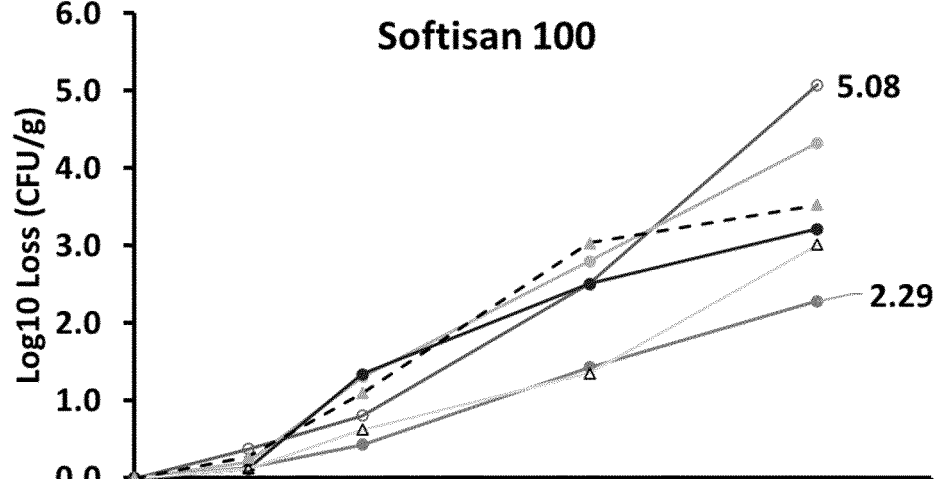
Figure 2:
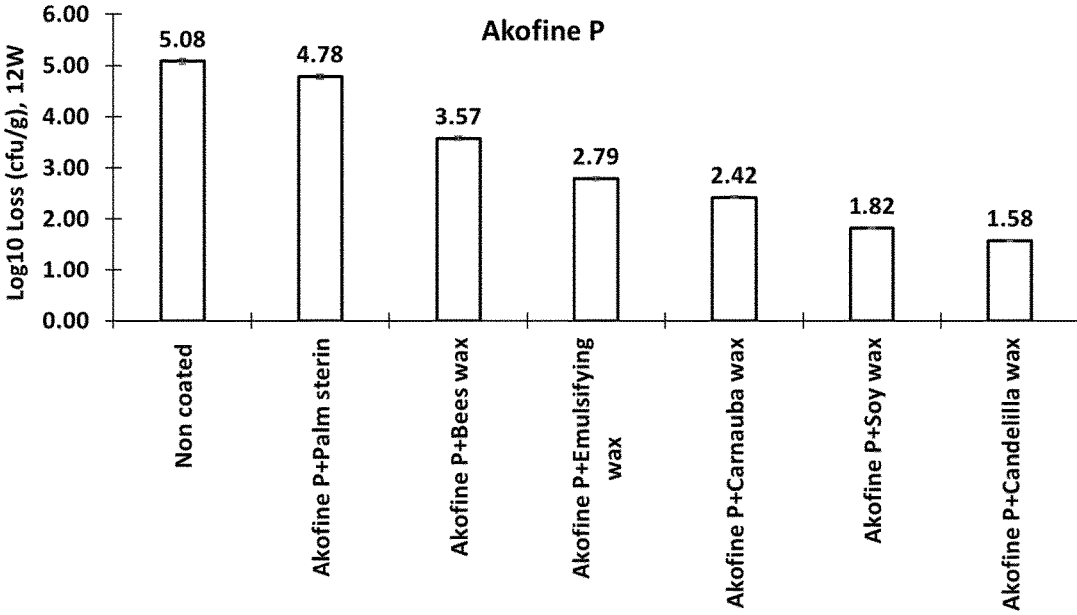
FIG. 2 is a graph comparing 12 weeks stability data of fat blends prepared by blending Akofine P™ with waxes for coating of cryoprotectant.

FIG. 2 is a graph comparing 12 weeks stability data of fat blends prepared by blending Akofine P™ with waxes for coating of CP to achieve stability at $a_w=0.35$ and T=25° C. It is very clear from FIG. 1 and FIG. 2 that the selection of fat blend is crucial process to protect bacterial viability from higher water activity. The non-coated CP has 5.08 $Log_{10}$ Loss (CFU/g) after 12 weeks of storage at ambient conditions. All the coated CP with different fat blends has shown significantly lesser $Log_{10}$ losses compared to Non-coated CP. This shows the importance of coating in protecting bacteria from higher water activity which arises from the excipients. In FIG. 2, it can be seen that the fat blends prepared by blending Akofine P™-Soy wax and Akofine P™-Candelilla wax has only 1.85 and 1.58 $Log_{10}$ Loss (CFU/g) compared to non-coated CP (5.08 $Log_{10}$ Loss (CFU/g)). This could be due to the blending of two different hydrophobic matrices with different melting point for example, Akofine P™ which has melting point of 60° C. whereas soy wax has 67° C. and candelilla wax has 77° C. (cf. Table 5). The blending of hydrogenated fat with natural waxes forms a new blend which has different melting point, solidification temperature which is very important to determine the fat crystal formation and its packing. These new fat blends (Akofine P™—Soy wax and Akofine P™—Candelilla wax) has unique melting and solidification properties, therefore providing better protection to CP after coating when compared to the non-coated CP.

Figure 3:
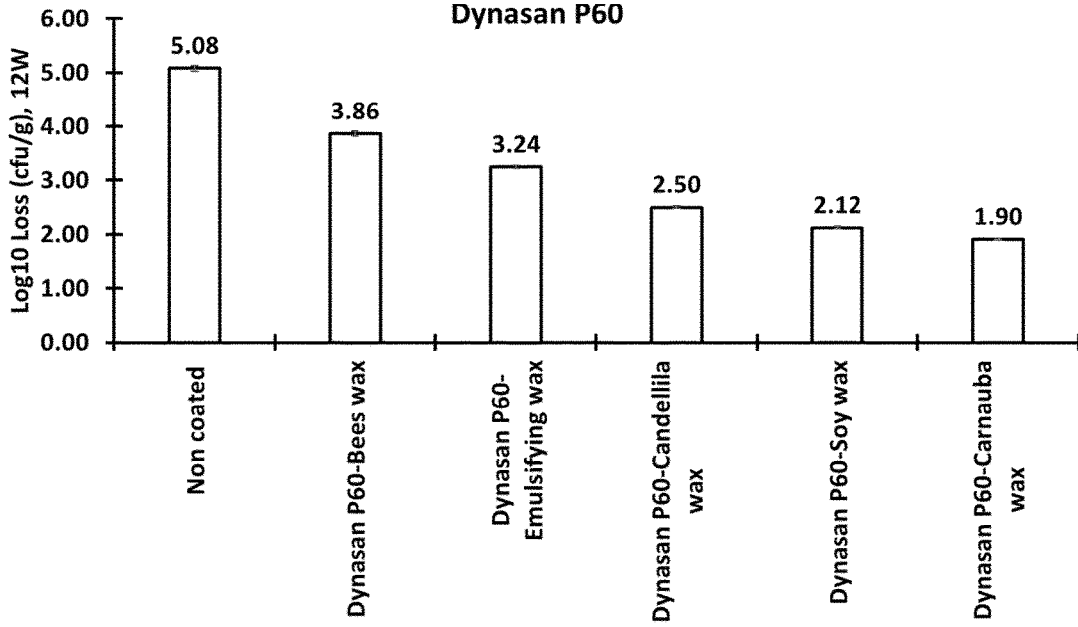
FIG. 3 is a graph comparing 12 weeks Stability data of fat blends prepared by blending Dynasan® P60 with waxes for coating of cryoprotectant.

FIG. 3 is a graph comparing 12 weeks Stability data of fat blends prepared by blending Dynasan® P60 with waxes for coating of CP to achieve stability at $a_w=0.35$ and T=25° C. Here, the effect of fat blends prepared by blending Dynasan® P60 with different waxes to coat CP to improve its ambient storage stability can be seen. The blend prepared using Dynasan® P60-Soy wax and Dynasan® P60-Candelilla wax has significantly lesser $Log_{10}$ Loss (CFU/g) compared to non-coated CP after 12 weeks at ambient storage conditions. The melting point after blending of Dynasan® P60 and Carnauba wax lies between 58 to 86° C. and this will also have an impact on the crystal formation and solidification properties and it lead to the better protection to CP at ambient storage conditions even after 12 weeks of storage. The fat blends prepared using HPFAD (FIG. 1B) and Softisan® 100 (FIG. 1D) with different waxes showed poor stability compared to other fat blends prepared using Akofine P™ (FIG. 1A) and Dynasan® P60 (FIG. 1C). This could be due to the poor crystal packing of fat blend that allowed the moisture migration from the excipient and led to decrease in viability.

Figure 4:
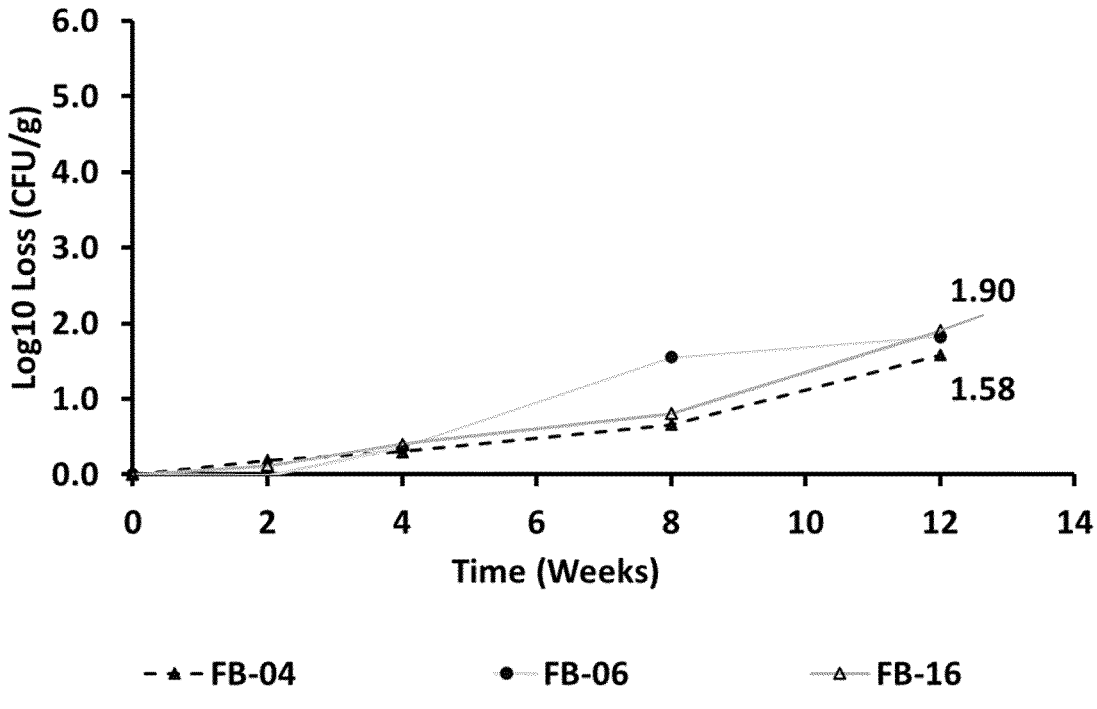
FIG. 4 is a graph comparing 12 weeks stability data of fat blends according to a preferred embodiment, used for coating of cryoprotectant.

FIG. 4 is a graph comparing 12 weeks stability data of preferred fat blends used for coating of CP to achieve stability at ambient storage conditions ($a_w$=0.35 and T=25° C.). It is very well demonstrated from the current study, that fat coating using suitable fat blend is important to achieve stability at ambient storage conditions ($a_w$=0.35 and T=25° C.). FIG. 1 showed the effect of different fat blends when used for coating on stability of CP at ambient storage conditions. Therefore, it was found that HPFAD and Softisan® 100 when blended with different waxes and used for coating has given poor storage stability. The blend prepared using Akofine P™ and Dynasan® P60 with waxes such as Soy wax, Carnauba wax and Candelilla wax has given better stability to CP at ambient storage conditions compared to the other blends used in this study. From FIG. 4, it is very clear that the Akofine P™ with Candelilla wax has a significantly better protection to the CP i.e. 1.58 $Log_{10}$ Loss (CFU/g) after 12 weeks of storage at ambient conditions. This could be due to the compatibility of Akofine P™ and Candelilla wax with CP.

Figures 5A, 5B:
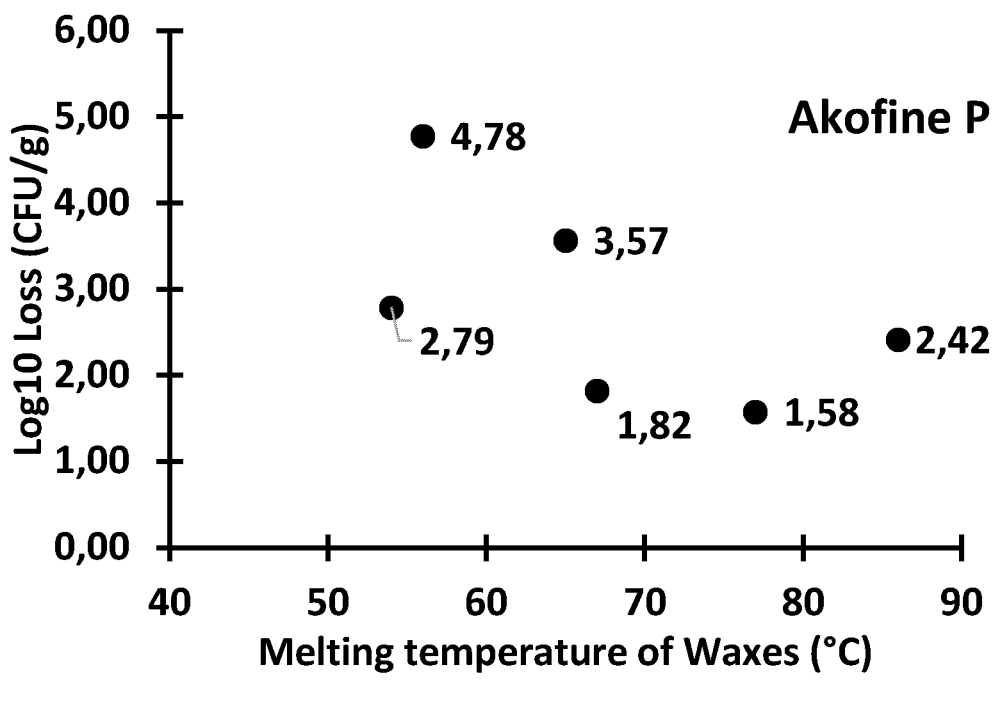
FIG. 5A-5D are graphs showing effect of melting temperatures of waxes used for blending with fats to coat cryoprotectants.
Figure 5C:
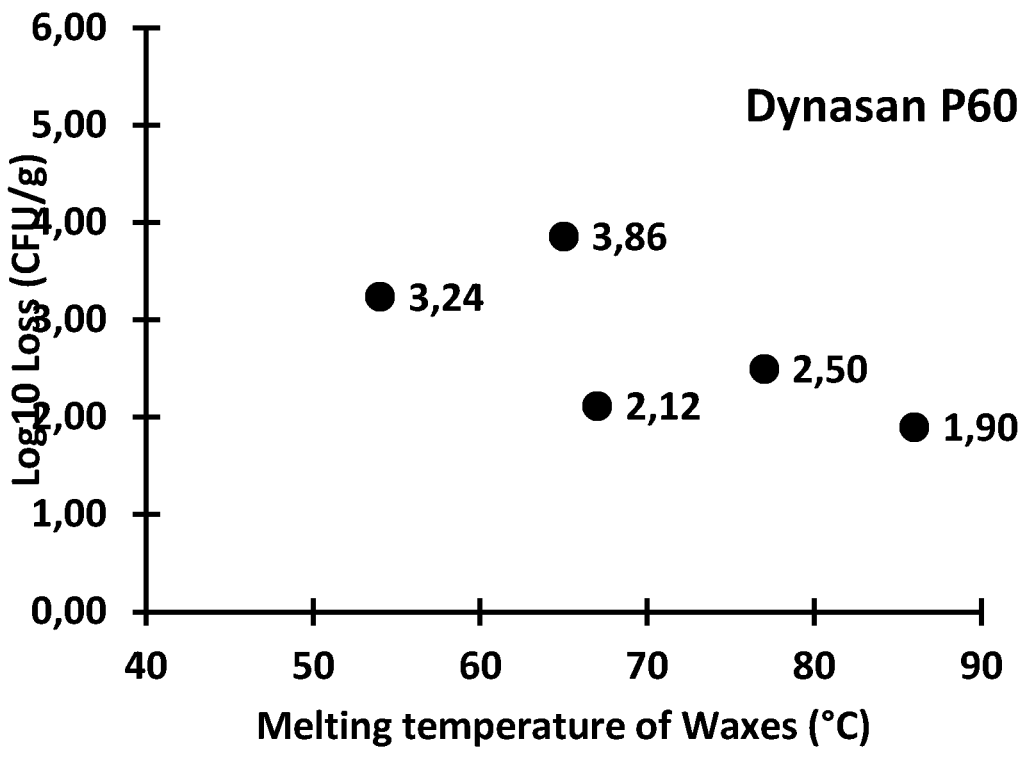
Figure 5D:
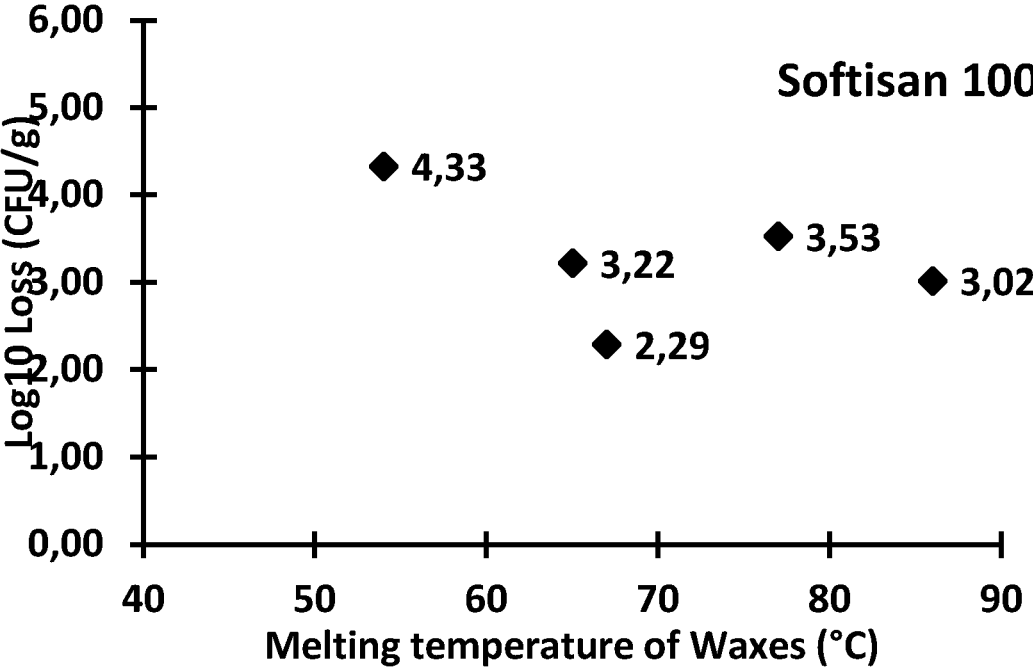

FIG. 5 shows effect of melting temperatures of waxes used for blending with fats to coat CP to achieve stability at ambient humid conditions. FIG. 5A shows data for Akofin P Akofin-P, FIG. 5B shows data for HPFAD, FIG. 5C shows data for Dynasan® P60, FIG. 5D shows data for Softisan® 100.

From FIG. 5, it was observed that the fat blends prepared using different waxes has important role in providing protection to the CP when stored at ambient humid conditions. For example, the fat blend prepared using Akofine P™ and waxes of different melting points, it was observed that high temperature melting wax blends has given better protection and cell viability during storage compare to the low temperature melting waxes. For example, Akofine P™ was blended with candelilla wax of melting point 77° C. has better protection during storage (1.58 $Log_{10}$ Loss (CFU/g) after 12 weeks) at ambient humid conditions (FIG. 5). This could be due to the blend prepared using high temperature melting waxes which forms a close fat crystal packing which will not allow moisture migration from the excipient easily to the core and thereby enhances the storage stability of CP. On the other hand, the fat was blended with the low temperature melting wax with melting temperature<60° C. has given poor protection to CP and thus resulted in poor cell viability when stored at ambient humid conditions (FIG. 5). The poor stability using low temperature melting wax could be due to the poor packing of fat crystals in fat blends which created micropores or microcapillaries in the coating to allow moisture migration from the excipient to core which thereby decreases cell viability.

Figure 17:
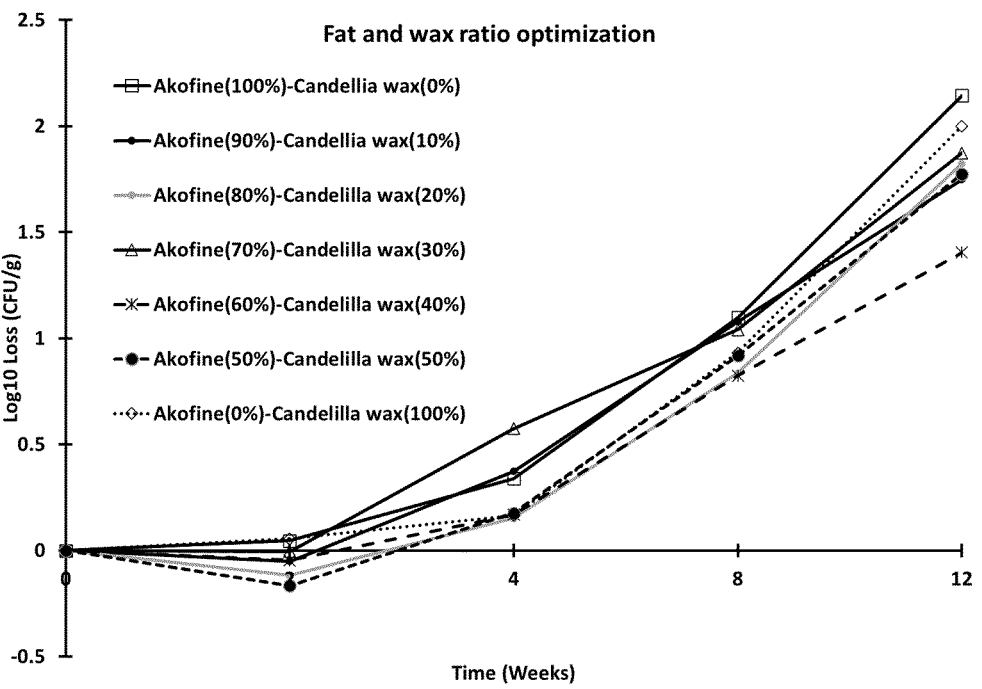
FIG. 17 is a graph showing optimization of a fat blend ratio for a mix according to a preferred embodiment (Akofine P™ and candellia wax).
Figure 18:
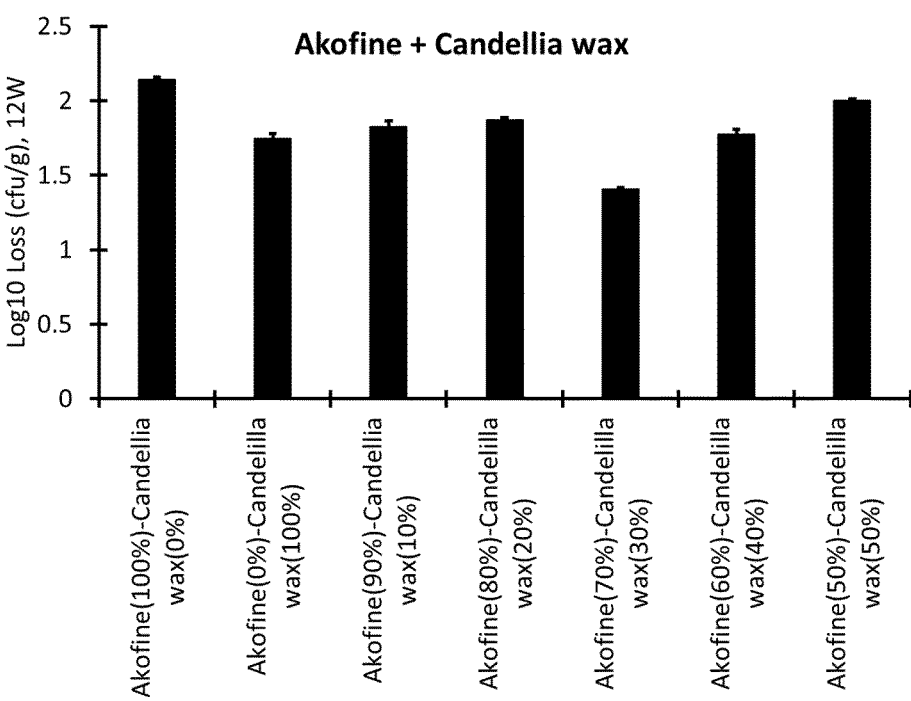
FIG. 18 is a graph showing effect of optimization of a fat blend ratio for a mix according to a preferred embodiment (Akofine P™ and candellia wax) on the viability after 12 weeks of storage at ambient humid conditions.

FIG. 17 and FIG. 18 show the effect of mixing ratios of hydrogenated palm oil and candelilla wax as a fat coating material to coat CP to provide barrier for moisture migration from excipient ($CaCO_3$) during storage (T=25° C.; $a_w$=0.35 and 12 weeks). The hydrogenated palm oil and candelilla wax alone could not able to provide significant protection to the CP at ambient humid conditions even though both of them are high melting products. The $Log_{10}$ Loss (CFU/g) for hydrogenated palm oil and candelilla wax were 2.1 and 2.0 respectively after 12 weeks of storages. The hydrogenated palm oil and candelilla wax blends had better protection to CP compared to their pure forms. When the blending of hydrogenated palm oil and candelilla wax were carried out ranging from 50 to 90%, 1.4 to 1.87 $Log_{10}$ Loss (CFU/g) were observed after 12 weeks of storage at ambient humid conditions. These results suggests that optimal blending ratios of hydrogenated palm oil and candelilla wax is required to achieve synergy between two which can provide optimal crystal packing and better fat coating to enhance the protection to CP during storage at ambient humid conditions. The optimal ratios for hydrogenated palm oil (60%) and candelilla wax (40%) provided better protection to CP i.e. 1.4 Log 10 Loss (CFU/g) after 12 weeks of storage at ambient humid conditions compared to their individual forms.

CONCLUSION

Example 1 describes the method of use of compatible fat coating blend prepared by mixing suitable fat and waxes with defined melting point to coat CP to enhance the storage stability of LAB at ambient humid conditions (T=25° C.; $a_w$=0.35). The fat blend prepared using Akofine P™ and Candelilla wax showed 1.58 $Log_{10}$ Loss (CFU/g) after 12 weeks of storage at ambient conditions when used for coating CP. This can be compared to stability of a non-coated cryoprotectant, which was 5.08 $Log_{10}$ Loss (CFU/g). Thus, the results of this study suggested that the blending of suitable fat i.e. Akofine P™ with high temperature melting wax such as Candelilla wax which has new melting point and fat crystallization properties when used for coating CP provide improved microbial stabilization at ambient humid conditions (T=25° C.; $a_w$=0.35).

Example 2: Bulk Density of Cryoprotectants

A fat coated (microencapsulated) probiotic product, such as presented in Example 1, has two main aspects: (1) The 'core', which is actually dried powder particles of certain size, for example, the dry powder particles obtained after milling and sieving of freeze-dried granulate, and (2) The 'coating', which is applied on top of the core particles to create a barrier for water molecules.

Traditionally, it was thought that if a fat coating is deposited on any type of core, it should impart stability to the active ingredients (such as probiotic cells) entrapped in the core and it should not matter that much on what type of core does one uses. However, in the present study we found out that for the same type of fat coating, varying stability was obtained for different compositions of the core. In this example, a particular combination of core and coating is shown, resulting in much better stability of probiotics under humid ambient conditions. Thus, a mixture of certain cryo-additive (cryoprotectant/core) types, based on for example their bulk densities, results in better probiotic stability.

In this Example 2, the viability protective effect of core cryos with lesser bulk densities of cryoprotectants and their compatibility with the fat to improve the storage stability of LAB at ambient humid conditions (T=25° C. and $a_w$=0.35) is demonstrated. Core cryos with bulk density of 183 kg/m3 showed 1.50 log loss (cfu/g) compared to reference cryo with bulk density of 271 kg/m3 which showed 4.78 log loss (cfu/g) after 12 weeks of ambient humid storage.

Fresh *Lactobacillus animalis* (LA51) cell concentrate was produced as set out in Example 1. The cryoprotectant-1 (CP-1) formulation is the current benchmark reference. All the core cryoprotectants were prepared as given in Table 6, according to the process set out in Example 1. These cryoprotectants were used to study the effect of fat coating on the viability of LA51 at ambient humid condition (T=25° C. and aw=0.35).

TABLE 6

| Sr. No. | Ingredients | CP-1 | CP-2 | CP-3 | CP-4 | CP-5 |
|---|---|---|---|---|---|---|
| | The composition of cryoprotectants (% w/w) used for fat coating. | | | | | |
| 1 | Maltodextrin DE12 | 5.00 | 5.00 | 11.85 | 7.93 | 7.62 |
| 2 | Oligofructose | — | — | 11.85 | 7.93 | 7.62 |
| 3 | Trehalose | 23.00 | 23.00 | — | — | — |
| 4 | Pectin A | — | — | 0.30 | — | — |
| 5 | Pectin C | — | — | — | 0.68 | 0.66 |
| 6 | HiCap ® (OSA starch) | — | — | — | — | 2.41 |
| 7 | Xanthan Gum | — | — | — | 0.27 | 0.25 |
| 8 | Sodium ascorbate | — | 5.00 | 4.29 | 3 | 3.31 |
| 9 | Tri-sodium Citrate | 5.00 | — | — | | |
| 10 | RO water | 67.00 | 67.00 | 71.71 | 80.19 | 78.12 |

After pelletization of these cryo-formulations containing LA51 in liquid nitrogen, the pre-freeze dried (PFD) powder were freeze dried using safe profile at 32° C., 0.3 mbar. The freeze dried (FD) powder (granulates) were subjected for grinding and sieving to get a fine grinded FD-cryo powder with particle size close to 60 mesh (250 μm). The bulk densities of cryoprotectant powders were determined as described in U.S. pharmacopoeia (org/harmonization-standards/pdg/general-chapters/bulk-density-and-tapped-density-of-powers).

These cryoprotectant powders were blended with an excipient calcium carbonate ($CaCO_3$) having the water activity (aw) of 0.35. The blends were prepared by mixing 1 part of finely grinded cryo powder with 24 parts of $CaCO_3$ ($a_w$=0.35). These blends of cryoprotectant powder with $CaCO_3$ were subjected to stability chamber maintained at 25° C. to check their storage stability. The $a_w$ of the final blend (cryoprotectant powder and $CaCO_3$) were determined to ensure achievement of correct $a_w$ i.e. 0.35. The samples were withdrawn at predetermined time intervals and analyzed for CFU/g to give the viability of microbial cultures under storage. In the next set, the FD cryoprotectant powders were coated with a fat using fat pelletization process according to Example 1. The fat mixture as shown in Table 7 was molten by heating the contents at 70° C. for 15 min. The FD cryo powder was dispersed into the molten fat and homogenized for 5 min using rotor stator homogenizer. The homogenized molten mixture was dripped on the stainless steel (SS) sheet which was maintained at 23° C. for 1 min which allowed the molten fat to solidify. Finally, the fat powder were recovered from the SS sheet and stored in the refrigerator until its further use.

TABLE 7

| Sr. No. | Ingredients | Composition (%, w/w) |
|---|---|---|
| | Fat mixture used for fat coating of cryoprotectant powders. | |
| 1 | Hydrogenated Palm oil | 64 |
| 2 | Palm Stearin | 16 |
| 3 | Cryoprotectant Powder | 20 |

The fat powder of different cryoprotectants were blended into $CaCO_3$ of aw=0.35 (1 g of fat powder:24 g of $CaCO_3$). In this process, the mixture of fat powder and $CaCO_3$ were grinded to achieve the uniform size (60 mesh, 250 μm) of the fat powder to that of the $CaCO_3$. The mixture of fat powder and $CaCO_3$ were packed into the Alu-pouches and stored at 25° C. in stability chamber. The samples were withdrawn at predetermined time intervals and analyzed for CFU/g. For conducting the CFU analysis, the fat coated samples were allowed to decapsulate using decapsulation buffer (Maximum Recovery Diluent supplemented with 1.0% Tween 80). The $CaCO_3$ blended fat coated sample was weighed and transferred to stomacher bag containing decapsulation buffer. This mixture was allowed to stomach using stomacher at normal speed for 2 min. Then the stomacher bag containing sample was incubated at 37° C. for 30 min in incubator. After incubation, the stomacher bag was again allowed to stomach at normal speed for 2 min. Sample from stomacher bag was taken for CFU analysis using serial dilution method.

Figure 6:
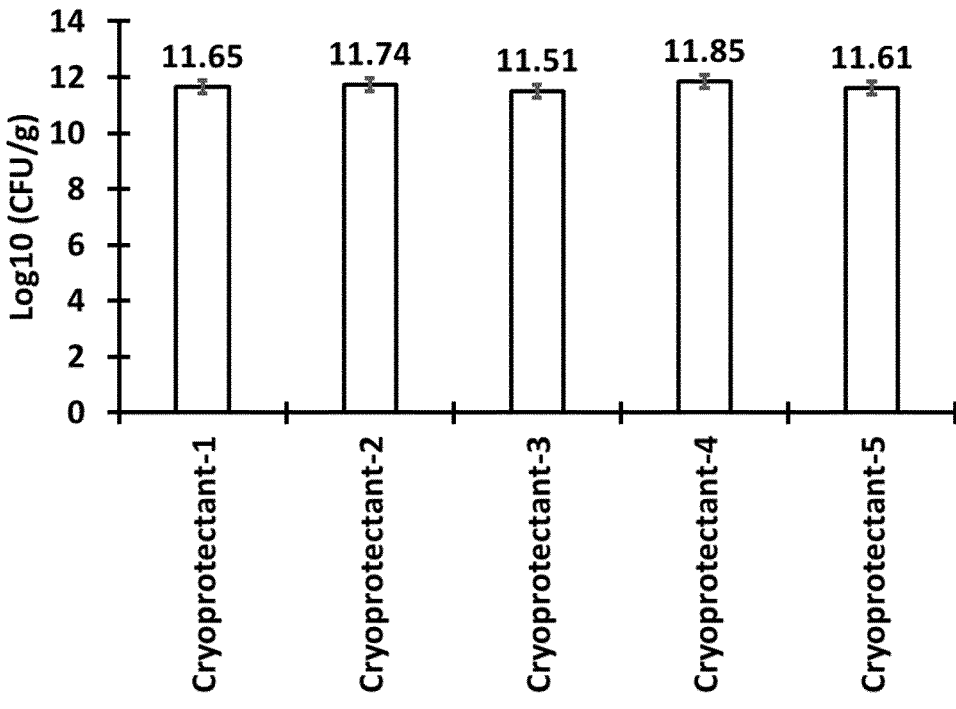
FIG. 6 is a graph showing process stability of freeze dried cryo-formulations according to various embodiments.

FIG. 6 is a graph showing process stability of FD cryo-formulations of LA51. It is essential to add the mixture of cryoprotectant additives to protect the LAB during freeze drying step. The FIG. 6 shows effect of addition of different cryoprotectants on the viability of LA51 cells during drying step.

Figure 7:
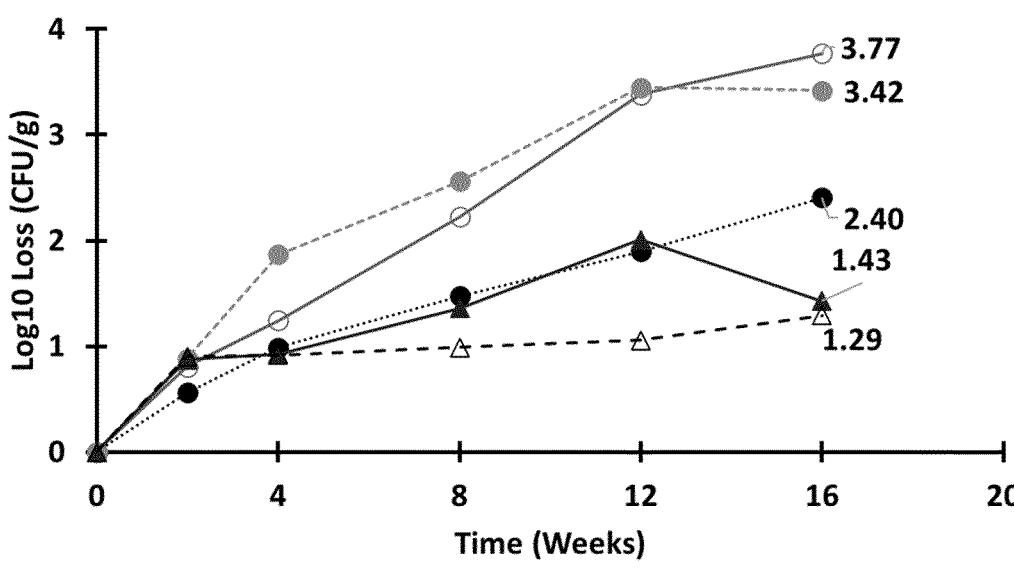
FIG. 7 is a graph showing stability of freeze dried cryo-formulations according to alternative embodiments.

FIG. 7 is a graph showing stability of FD cryo-formulations of LA51 at accelerated storage conditions (T=37° C.; $a_w$=0.05). FIG. 7 shows the storage stability of LA51 FD granulates prepared using 5 different cryoprotectants as mentioned in Table 6. In this study, the CP 1 and CP 2 were used as reference cryoprotectants to investigate the role of other cryoprotectants during storage stability of LA51. The CP 1 to CP 3 has shown more than 2 log CFU/g of reduction when they were stored at accelerated conditions (T=37° C.; aw=0.05) for 16 weeks. However, the CP 4 and CP 5 were most compatible cryoprotectants which showed better protection with only 1.43 and 1.29 log CFU/g reduction respectively (FIG. 7). This could be due to the mixture of cryoadditives in cryoprotectants which are not only responsible to provide the process stability but also storage stability.

Figure 8:
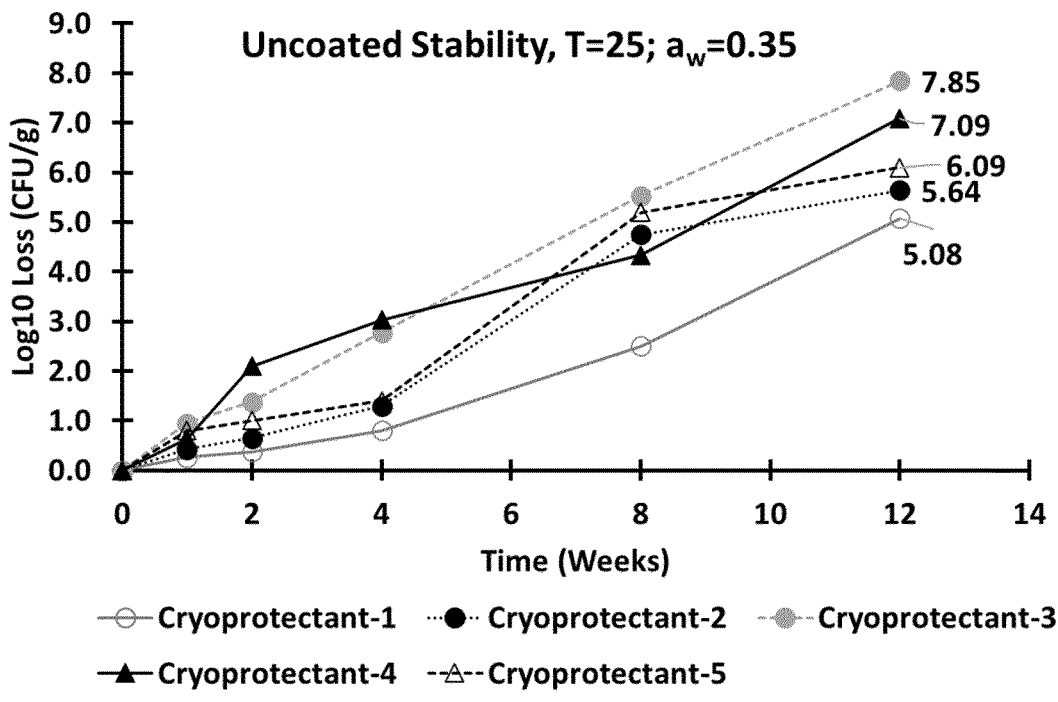
FIG. 8 is a graph showing stability of milled cryo-formulations according to various embodiments.

FIG. 8 is a graph showing stability of milled cryo-formulations of LA51 blended with $CaCO_3$ ambient storage conditions (T=25° C.; $a_w$=0.35).

The cryoprotectants containing LA51 were ground to get a fine powder (5250 micron). These cryoprotectant formulations were blended 25 times with the $CaCO_3$. In this study, the fine calcium carbonate powder was used as an excipient which has water activity ($a_w$) around 0.35. The aim of this study was to investigate the effect of aw on the storage stability of LA51. The various cryo-protectants studied showed more than 5 log CFU/g reduction after 12 weeks of storage at ambient humid conditions (FIG. 8).

Figure 9:
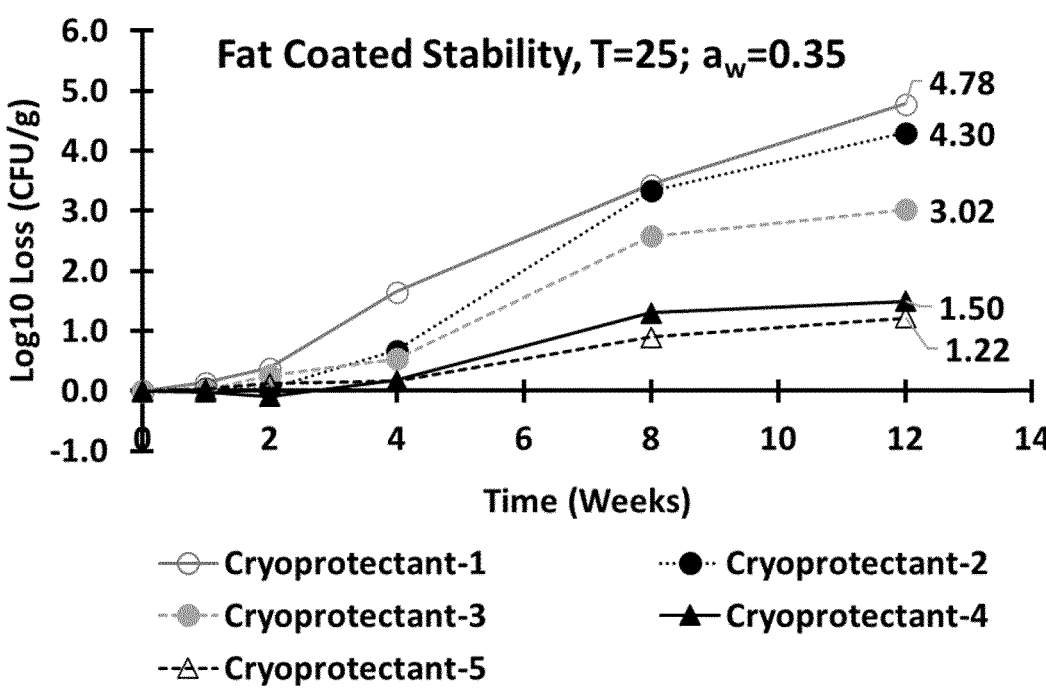
FIG. 9 is a graph showing stability of fat coated cryo-formulations according to alternative embodiments.

FIG. 9 is a graph showing stability of fat coated cryo-formulations of LA51 blended with $CaCO_3$ at ambient storage conditions (T=25° C.; aw=0.35).

In the present study, it was found that compatibility of various cryoprotectants with fat is very important to have a better packing effect, to get uniform coating over the cryo formulations. All the 5 cryoprotectants were coated with hydrogenated vegetable fat using fat palletization process. It was observed from FIG. 9 that with fat coating over the cryoprotectant 4 and cryoprotectant 5, there were only 1.50 and 1.22 log CFU/g reduction respectively after 12 weeks of storage (T=25° C.; aw=0.35). But the same effect has not been observed in case of CP-1 to CP-3.

Figure 10:
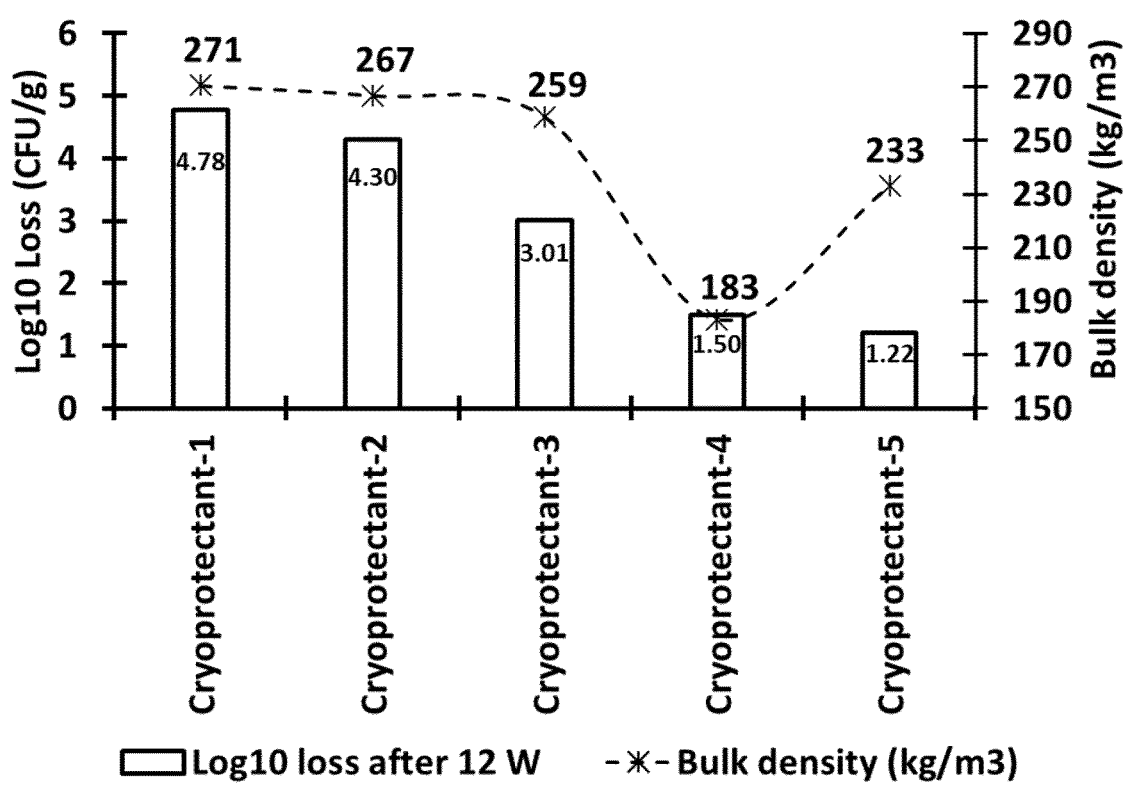
FIG. 10 is a graph showing effect of bulk density (kg/m$^3$) of cryoformulations according to various embodiments.

FIG. 10 is a graph showing effect of bulk density ($kg/m^3$) of cryoformulations on Log loss CFU/g after 12 weeks of ambient humid storage.

Figure 11:
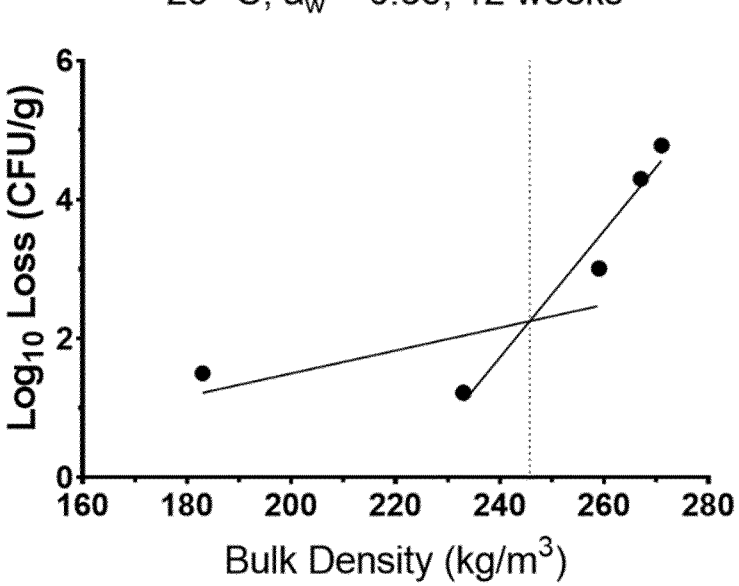
FIG. 11 is a graph showing bulk density (kg/m$^3$) Vs Log$_{10}$ Loss (CFU/g) of cryoformulations according to various embodiments, after 12 weeks of ambient humid storage.

The role of CP-4 and CP-5 in providing higher viability at ambient humid condition was further investigated by determining the physical properties of cryoprotectants. Bulk density is defined as the mass of the many particles of the material divided by the total volume they occupy. The total volume includes particle volume, inter-particle void volume, and internal pore volume. FIG. 10 and FIG. 11 clearly demonstrated that the lower bulk density cryoprotectants had higher viability protection after 12 week of storage at ambient humid conditions when coated with fat. The CP 4 and CP 5 has bulk densities lower than reference cryo (CP-1) i.e. 32% and 13% respectively which has direct impact on packing between cryo particles and fat thereby suggesting higher viability protection upon storage. Therefore, the coated CP 4 and CP 5 has shown highly significant viability protection (1.5 and 1.2 Log 10 loss (CFU/g)) compared to reference cryo (CP-1, 4.78 Log loss) after 12 weeks of storage at ambient conditions (T=25° C.; $a_w$=0.35).

Figure 12:
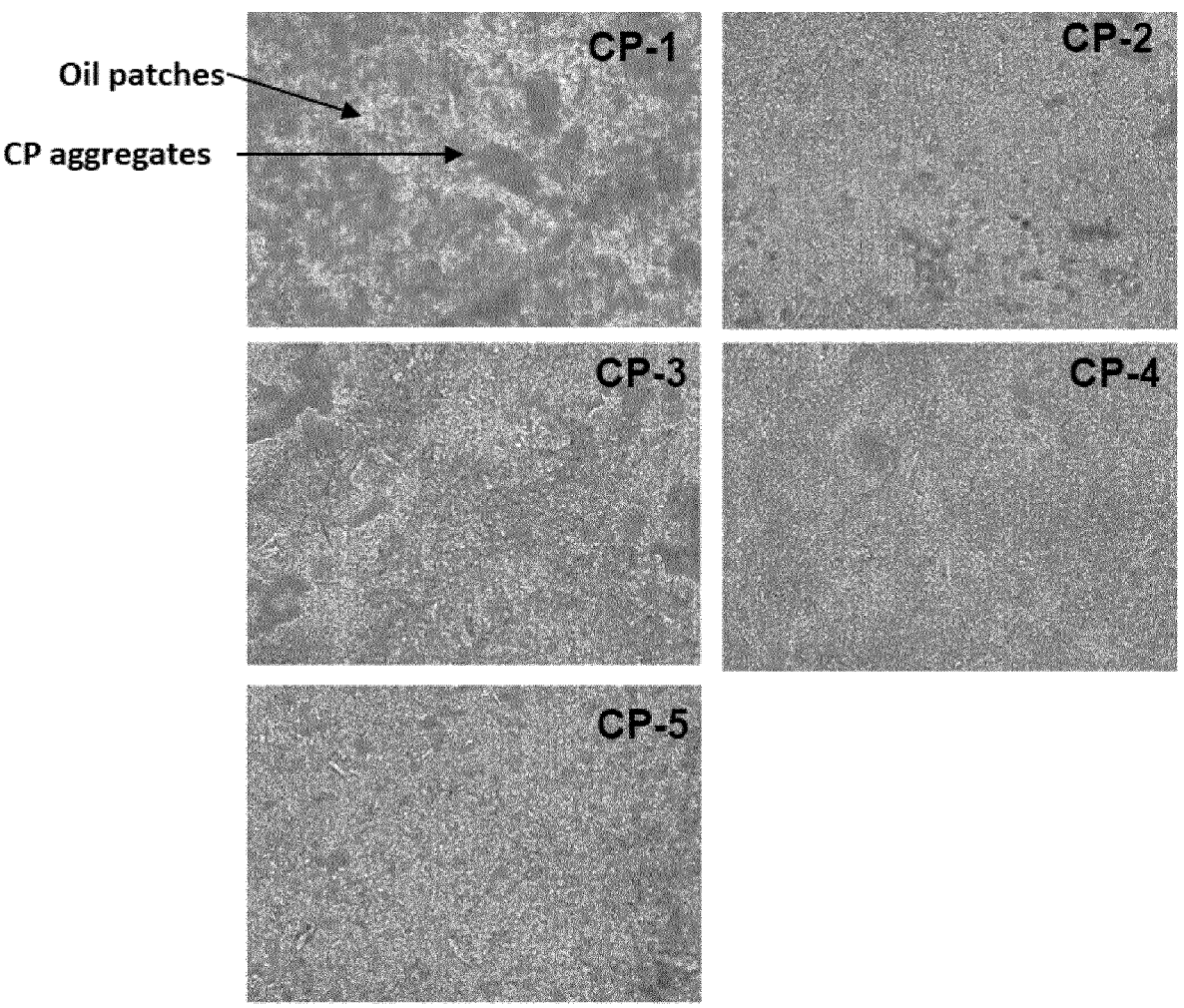
FIG. 12 is a collection of microscopic images (Magnification 20×) of cryoprotectant dispersions according to various embodiments, in sunflower oil.

Microscopic imaging was performed to investigate the packing of cryoprotectants and their dispersibility in fat or oil. FIG. 12 are microscopic images (Magnification 20×) of cryoprotectant (CP) dispersions in sunflower oil. It was observed from the images (FIG. 12), CP 4 and CP 5 has uniform dispersion and packing in sunflower oil compared to the dispersion of CP 1. This phenomena could be due to the affinity of cryoadditives in CP 4 and CP 5 towards fats or oil, this has led to better particle packing and thereby resulted in better stability.

CONCLUSION

The present Example 2 describes the method of use of compatible cryoprotectant (core) with defined bulk densities with fat coating to enhance the storage stability of LAB at ambient humid conditions (T=25° C.; aw=0.35). CP 4 with bulk density of 183 kg/m3 showed 1.50 log loss (cfu/g) compared to CP 1 with bulk density of 271 kg/m3 which showed 4.78 log loss (cfu/g) after 12 weeks of ambient humid storage. The results of this study suggested that the integrated approach of combining the cryoprotectant with defined bulk density and fat coating may provide the solution of microbial stabilization at ambient humid conditions (T=25° C.; aw=0.35).

Example 3: pH and Water Effect on Stability

An experiment was designed to test how pH correlated to stability. In this Example 3, results indicate that optimizing acidifying activity induced by cryoprotectants determined as ΔpH (the difference between pH just after adding cryoprotectants to the cells and the pH after 2 h of holding at 10° C.) may enhance the shelf stability of dried microorganism after fat coating. There was 0.07 CFU/g $Log_{10}$ loss after 12 weeks at the ambient humid conditions (T=25° C. with aw=0.35) when ΔpH was 1.0, as compared to 3.56 and 4.80 CFU/g $Log_{10}$ loss in no/minimal acidifying activity (ΔpH=0.1) or very high acidifying activity cryoprotectants (ΔpH 2.5).

In order to investigate the role of cryoprotectants composition to provide viability protection, hydrophobic matter of cryoprotectants was determined. It can be seen that higher hydrophobic matter of cryoprotectants composition resulted in higher viability protection after 12 weeks of storage at the ambient humid conditions (T=25° C. with aw=0.35). Hydrophobic matter of cryoprotectants composition is defined as amount of dry matter reduced when 1:1 cryoprotectants and hydrocarbon (hexadecane) was mixed and kept overnight. The amount of cryoprotectants ingredient partitioned into the hydrocarbon is termed as percent hydrophobic matter of a cryoprotectants composition. The cryoprotectants core optimized with hydrophobic matter of 3% followed by fat coating showed very high viability protection. This is a novel concept and holds great importance for the CH cultures and probiotic to provide higher water activity microbial stabilization solution.

a. Production of Cells and Cryoformulations

Fresh *Lactobacillus animalis* (LA51) cell concentrate was produced as set out in Example 1. A total of 9 cryoprotectant (CP-1 to 9) formulation as mentioned in Table 8 and freezedried biomass without cryoprotectant were tested. CP-1 containing trehalose, maltodextrin and ascorbate was used as a benchmark/reference in the current study for the comparison with new cryoprotectants formulation (CP-02 to CP-09). All the cryoprotectants were prepared as given in Table 8. These cryoprotectants were mixed with LA51 cell mass. After palletization of these cryoformulations containing LA51 in liquid nitrogen, the pre-freeze dried (PFD) powder were freeze dried using at 32° C., 0.3 mbar. The PFD's of individual samples were loaded into a labelled pre-frozen metal container and the containers were transferred to a freeze dryer. The PFDs were dried using a Martin Christ freeze dryer (Germany, GmbH) for 26 h. The freeze dried (FD) powder (granulates) were subjected for grinding and sieving to get a fine grinded cryoprotectants powder with particle size close to 60 mesh (250 μm). The cryoprotectant powders were coated with a fat using fat palletization process. The fat mixture as shown in Table 9 was melted by heating the contents at 70° C. for 15 min. The cryoprotectants powder was dispersed into the molten fat and homogenized for 5 min using rotor stator homogenizer. The homogenized molten mixture was dripped on the stainless steel (SS) sheet which was maintained at 23° C. for 1 min which allowed the molten fat to solidify. Finally, the fat powder were recovered from the SS sheet and stored in the refrigerator (4-10° C.) until its further use.

TABLE 8

Composition of cryoprotectants formulations.

| | | % w/w | | | | | | | | |
|---|---|---|---|---|---|---|---|---|---|---|
| No. | Ingredients | CP-01 | CP-02 | CP-03 | CP-04 | CP-05 | CP-06 | CP-07 | CP-08 | CP-09 |
| 1 | Trehalose | 5 | | 12 | | | | | | |
| 2 | Maltodextrin | 19 | | | 11.85 | | | 11.15 | 10 | 15 |
| 3 | Skimmed milk | | 12 | | | | | | | |
| 4 | Lactose | | 12 | | | | | | | |
| 5 | FOS | | | 12 | 11.85 | | 12 | 11.15 | 10 | 5 |
| 6 | Pectin | | | | 0.3 | | | 0.2 | 0.8 | 0.5 |
| 7 | Inulin | | | | | 12 | | | | |
| 8 | Sucrose | | | | | 12 | 12 | | | |
| 9 | $KH_2PO_4$ | | | | | | | 1.5 | 1 | |
| 10 | $CaCO_3$ | | | | | | | | 0.1 | 0.1 |
| 11 | Na-ascorbate | 6 | 6 | 6 | 6 | 6 | 6 | 6 | 6 | 6 |
| 12 | RO-Water | 70 | 70 | 70 | 70 | 70 | 70 | 70 | 70 | 70 |
| 13 | Dry Matter (%, w/w) | 30 | 30 | 30 | 30 | 30 | 30 | 30 | 30 | 30 |

TABLE 9

Fat mixture used for fat coating of cryoprotectant powders.

| Sr. No. | Ingredients | Composition (%, w/w) |
|---|---|---|
| 1 | Hydrogenated Palm oil | 64 |
| 2 | Palm Stearin | 16 |
| 3 | Cryoprotectant Powder | 20 |

The fat powder of different cryoprotectants were blended into $CaCO_3$ of $a_w$=0.35 (1 g of fat powder:24 g of $CaCO_3$). Next, the mixture of fat powder and $CaCO_3$ were grinded (milled) to achieve the uniform size (60 mesh, 250 μm) of the fat powder to that of the $CaCO_3$. The mixture of fat powder and $CaCO_3$ were packed into the Alu-pouches and stored at 25° C. in stability chamber. The samples were withdrawn at predetermined time intervals and analyzed for CFU/g. For conducting the CFU analysis, the fat coated samples were allowed to decapsulate using decapsulation buffer (Maximum Recovery Diluent supplemented with 1.0% Tween 80). The $CaCO_3$ blended fat coated sample was weighed and transferred to stomacher bag containing decapsulation buffer. This mixture was allowed to stomach using stomacher at normal speed for 2 min. Then the stomacher bag containing sample was incubated at 37° C. for 30 min in incubator. After incubation, the stomacher bag was again allowed to stomach at normal speed for 2 min. Sample from stomacher bag was taken for CFU analysis using serial dilution method.

TABLE 10

Colony forming unit (CFU) and Flowcytometry results of different cryoprotectants (aw ≤ 0.05).

| No. | Cryoprotectants | CFU/g | Active count/g | % Active count | Water Activity ($a_w$) |
|---|---|---|---|---|---|
| 1 | Biomass Control | 6.25E+11 | 1.17E+12 | 82.75 | 0.04 |
| 2 | CP-01 | 3.25E+11 | 6.99E+11 | 88.04 | 0.05 |
| 3 | CP-02 | 5.25E+11 | 9.75E+11 | 90.96 | 0.03 |
| 4 | CP-03 | 3.55E+11 | 5.82E+11 | 71.73 | 0.04 |
| 5 | CP-04 | 4.10E+11 | 5.96E+11 | 81.70 | 0.05 |
| 6 | CP-05 | 3.00E+11 | 5.60E+11 | 68.35 | 0.06 |
| 7 | CP-06 | 3.45E+11 | 7.20E+11 | 79.00 | 0.03 |

TABLE 10-continued

Colony forming unit (CFU) and Flowcytometry results of different cryoprotectants (aw ≤ 0.05).

| No. | Cryoprotectants | CFU/g | Active count/g | % Active count | Water Activity ($a_w$) |
|---|---|---|---|---|---|
| 8 | CP-07 | 1.55E+11 | 5.09E+11 | 70.16 | 0.05 |
| 9 | CP-08 | 3.80E+11 | 5.64E+11 | 76.21 | 0.04 |
| 10 | CP-09 | 4.25E+11 | 4.23E+11 | 76.24 | 0.05 |

TABLE 11

Colony forming unit (CFU) and water activities ($a_w$) of 1 g of fat coated cryoprotectants blended with 24 g of calcium carbonate ($CaCO_3$) to achieve target $a_w$ = 0.35.

| No. | Cryoprotectants | CFU/g | Water activity ($a_w$) |
|---|---|---|---|
| 1 | Biomass Control | 1.25E+09 | 0.32 |
| 2 | CP-01 | 3.00E+09 | 0.34 |
| 3 | CP-02 | 6.75E+08 | 0.33 |
| 4 | CP-03 | 3.30E+09 | 0.31 |
| 5 | CP-04 | 4.85E+08 | 0.33 |
| 6 | CP-05 | 3.60E+09 | 0.35 |
| 7 | CP-06 | 2.80E+09 | 0.32 |
| 8 | CP-07 | 2.50E+09 | 0.36 |
| 9 | CP-08 | 1.39E+09 | 0.33 |
| 10 | CP-09 | 3.95E+08 | 0.34 | b. Storage Stability Studies at Ambient Humid Conditions

Figure 13:
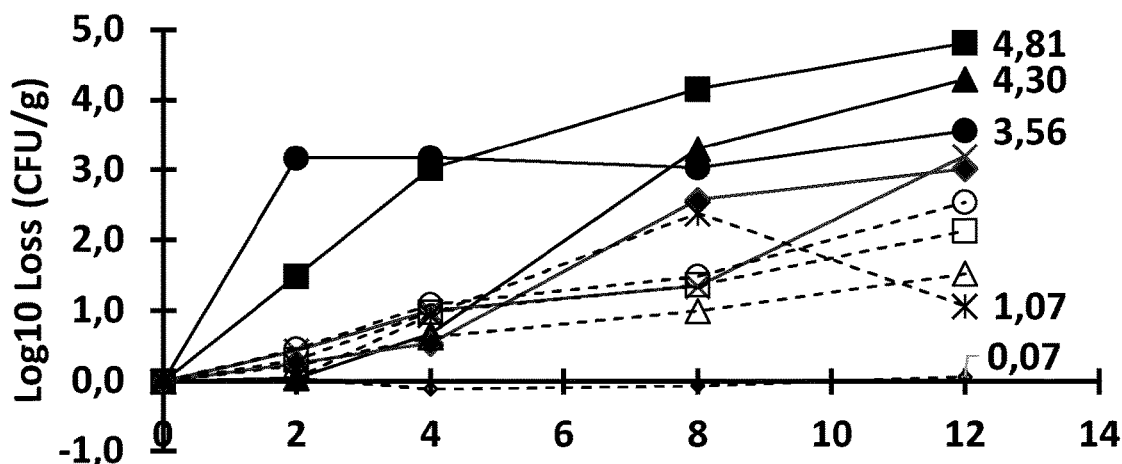
FIG. 13 is a graph showing storage stability curves of fat coated cryoprotectant powders according to various embodiments, after 12 weeks of ambient humid storage.
Figure 13:
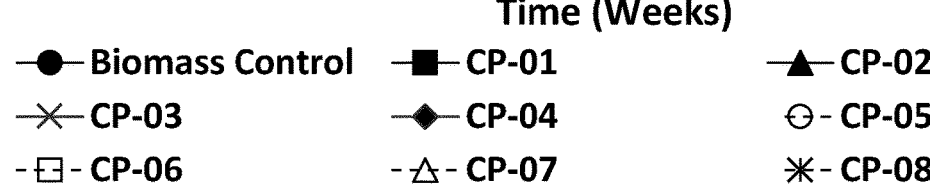

Table 10 represents the initial CFU/g, Active count/g and % Active count of FD-granulates of different cryoprotectants before grinding them into powders for coating purpose. Table 11 shows the initial CFU/g and water activities of blends of fat coated cryoprotectant powders and calcium carbonate ($CaCO_3$) before subjecting them to stability chamber. The FIG. 13 shows the storage stability curves of fat coated cryoprotectant powders at ambient storage conditions (T=25° C.; $a_w$=0.35). The FIG. 13 gives a clear indication of how important the role of cryoprotectant for fat coating to achieve the targeted stability at ambient humid storage conditions. It was observed that when there was no cryoprotectant with biomass upon fat coating, the Log 10 Loss (CFU/g) after 12 weeks of storage was 3.56. This could be due to lack of essential cryoprotectant around bacteria which not only give protection from osmotic stress during process but also helps them in uniformly dispersing into the molten fat to achieve uniform coating. Choosing right cryoprotectant is always a challenging task, the FIG. 13 is an evidence for such phenomena. When cryoprotectant CP-01 to CP-08 were chosen for microencapsulation of bacteria and thereby fat coating, the Log 10 Loss (CFU/g) after 12 weeks of storage were ranging from 1.07 to 4.81. Among all fat coated cryoprotectant, CP-09 showed a better stability (0.07 Log 10 Loss, CFU/g) after 12 weeks of storage at ambient humid condition.

c. Determination of Acidifying Properties of Cells During Formulation Step

Figure 14:
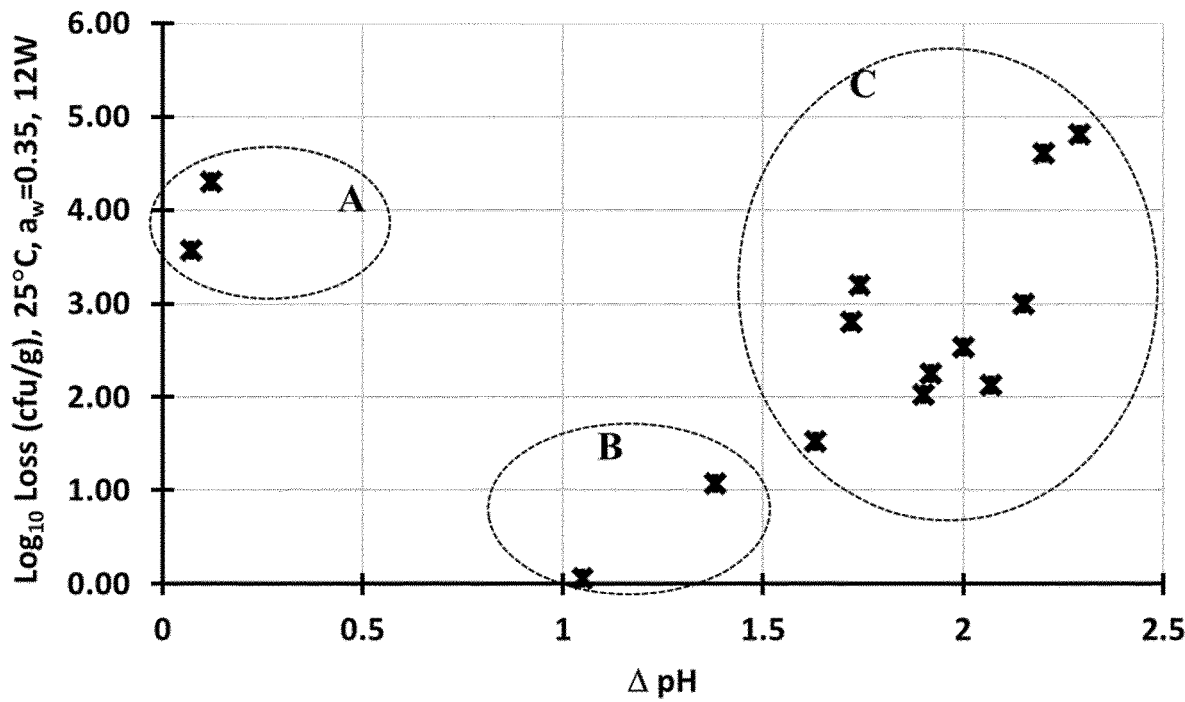
FIG. 14 is a graph showing the ΔpH effect of cryoprotectants in formulations according to embodiments, and corresponding impact on the viability.

After the cell separation step, cell concentrate was mixed with cryoprotectant and held at 10° C. for 2 hours. This time-step is referred as "holding time". This step is critical for the cell viability as cells are limited to nutrient and may enter to the cell starvation phase. It is observed that during holding time, cells metabolize and with the available sugars or hydrolysable carbohydrates, they produce some amount of organic acids which was noticed as a change in pH (Table 12). The difference between the pH measured after holding time and just after adding the cryoprotectants to the cells was termed as 'delta pH ($\Delta$pH)'. In this study, we have used only cells and not cryoprotectant in one group and 9 different cryoprotectant formulations as mentioned in Table 8. Delta pH was calculated and analyzed for the storage stability of cells after 12 weeks at the ambient humid conditions. It is noticed that when $\Delta$pH is very high (more than 3) or very low (less than 0.5) then the bacterial viability was minimal after 12 weeks of storage at the ambient humid conditions. However when $\Delta$pH was optimal (1 to 1.5) then the bacterial viability was maximum after 12 weeks of storage at the ambient humid conditions (FIG. 14). The cryoprotectants have an importance in protecting the LAB not only during freeze drying step but also it plays crucial role during their storage at ambient humid conditions. The FIG. 14 shows the $\Delta$pH effect of cryoprotectants at formulation step and their impact on the viability or Log 10 Loss (CFU/g) of LA51 cells in fat coated samples stored at ambient humid conditions after 12 weeks (T=25° C.; aw=0.35). From FIG. 13, it is very clear that the $\Delta$pH of cryoprotectant which can control the acidifying activity of LAB has a significant impact on protecting the LA51 cell along with fat coating at ambient humid conditions. Based on 12 weeks Log 10 Loss (CFU/g) results of fat coated cryoprotectant powders, they can be categorized into three different regions i.e. $\Delta$pH≤0.20 (region A, FIG. 14) with Log 10 Loss (CFU/g) ranging from 3.56 to 4.30; $\Delta$pH 1-1.50 (region B, FIG. 14) with Log 10 Loss (CFU/g) ranging from 0.07 to 1.07; $\Delta$pH≥1.50 (region C, FIG. 14) with Log 10 Loss (CFU/g) ranging from 1.53 to 4.81. This findings suggested that composition of cryoprotectants to control the acidifying property of cells during holding step is novel and inventive for microbial stabilization at ambient humid conditions.

TABLE 12

Determination of acidifying property of cells during holding time.

| No. | Cryoprotectants | Initial pH | pH after 2H | $\Delta$PH |
|---|---|---|---|---|
| 1 | Cells-Control | 7.09 | 7.02 | 0.07 |
| 2 | CP-01 | 6.92 | 4.63 | 2.29 |
| 3 | CP-02 | 6.72 | 6.6 | 0.12 |
| 4 | CP-03 | 6.84 | 5.1 | 1.74 |
| 5 | CP-04 | 6.83 | 4.68 | 2.15 |

TABLE 12-continued

Determination of acidifying property of cells during holding time.

| No. | Cryoprotectants | Initial pH | pH after 2H | $\Delta$PH |
|---|---|---|---|---|
| 6 | CP-05 | 6.79 | 4.79 | 2.00 |
| 7 | CP-06 | 6.81 | 4.74 | 2.07 |
| 8 | CP-07 | 6.76 | 5.13 | 1.63 |
| 9 | CP-08 | 6.82 | 5.44 | 1.38 |
| 10 | CP-09 | 6.87 | 5.82 | 1.05 | d. Determination of Hydrophobic Matter of Cryoprotectants

Figure 15:
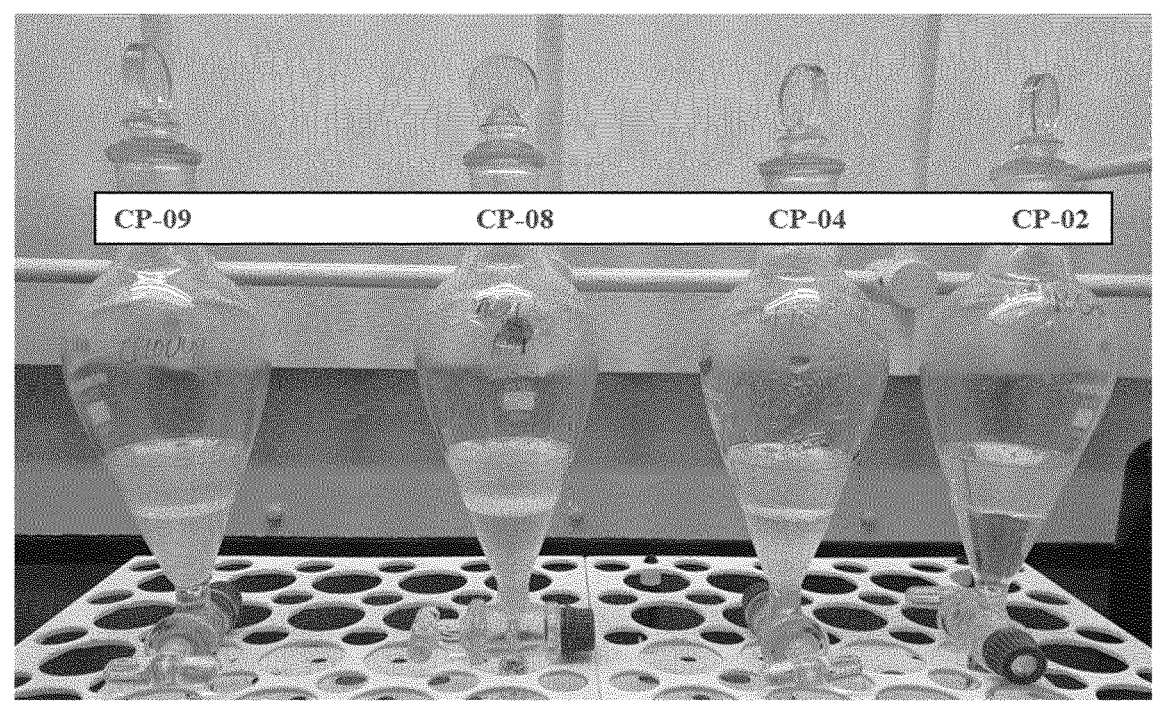
FIG. 15 is a photograph showing an experimental setup of cryoprotectants according to embodiments, partitioning from an organic layer (hexadecane).
Figure 16:
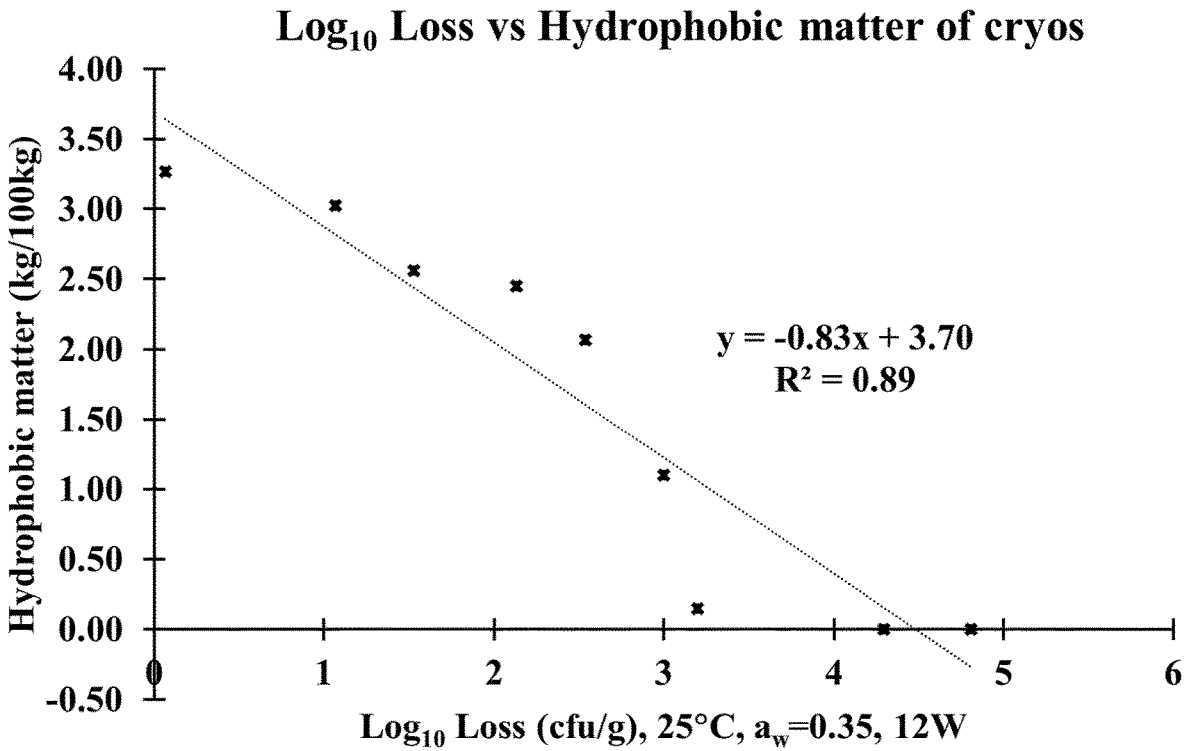
FIG. 16 is a graph showing effect of hydrophobic matter (kg/100 kg) of cryoprotectants according to various embodiments, on $Log_{10}$ Loss (CFU/g) after 12 weeks of ambient humid storage.

It is a hypothesis that the cryoprotectant with better compatibility and packing with fat coating are better in providing viability protection during ambient humid storage conditions. The compatibility of cryoprotectant with fat can be explained as their interactions with fat when coated. In this regards, experiment was performed to determine the hydrophobic matter/fraction in the cryoprotectant compositions by organic partitioning method. One part of cryoprotectant prepared and mentioned in Table 8 were mixed with one part of hexadecane in separating funnel and mixed thoroughly thrice for 2 minutes with 5 minutes rest each time. These funnels were stored at room temperature for overnight and then aqueous fraction was collected. It is evident from the FIG. 15 that the CP-02 had no partitioning and no interfacial layer whereas CP-09 had maximum partitioning with thick interfacial layer and hexadecane layer was visibly turbid (FIG. 15). Dry matter of cryoprotectant was determined before mixing with hexadecane and after mixing with hexadecane and stored overnight. Difference in the dry matter after hexadecane mixing of cryoprotectant composition was calculated as percent hydrophobic matter/fraction. The stability results clearly demonstrated that higher the hydrophobic matter better the stability (FIG. 16). This could be due to the better compatibility of cryoprotectant containing hydrophobic matter and thereby better packing in fat. This helped in preventing the moisture migration and thus showed maximum viability protection after 12 weeks of storage at the ambient humid storage conditions. Cryoprotectants CP-01 and CP-02 had no hydrophobic matter thus showed maximum CFU loss after 12 weeks whereas CP-09 had 3.26 hydrophobic matter and showed highest viability protection after 12 weeks of storage (Table 13).

TABLE 13

Hydrophobic matter/fraction of cryoprotectant vs Log10 Loss (cfu/g) after 12 weeks.

| No. | Cryoprotectants | Hydrophobic Matter (Kg/100 Kg) | $Log_{10}$ Loss (CFU/g) after 12 weeks |
|---|---|---|---|
| 1 | Biomass Control | Not applicable | 3.56 |
| 2 | CP-01 | 0.00 | 4.81 |
| 3 | CP-02 | 0.00 | 4.30 |
| 4 | CP-03 | 0.15 | 3.20 |
| 5 | CP-04 | 1.10 | 3.00 |
| 6 | CP-05 | 2.07 | 2.54 |
| 7 | CP-06 | 2.45 | 2.13 |
| 8 | CP-07 | 2.56 | 1.53 |
| 9 | CP-08 | 3.02 | 1.07 |
| 10 | CP-09 | 3.26 | 0.07 |

CONCLUSION

The finding of this study suggested that role of cryoprotectant powders coated with fat may be an approach to stabilize the microbes at ambient humid conditions. Further, the selection of a cryoprotectant with optimal hydrophobic matter added to the cells during freezing and drying followed by the fat coating is novel and inventive step to stabilize microbes at ambient humid conditions. CP-09 containing maltodextrin, FOS, pectin, calcium carbonate and ascorbate was the most effective cryoprotectant composition which also had maximum hydrophobic matter. The CP-09 is an example of integration of optimal ΔpH and hydrophobic matter of cryoprotectant when coated with fat for an enhanced storage stability of probiotic and LAB at ambient humid conditions.

The invention claimed is:

1. A method for the preparation of a composition comprising a microencapsulated microbial culture, said method comprising the steps of:
   a) obtaining a concentrated cell mass of the microbial culture;
   b) adding a protective compound to the concentrated cell mass of (a) to obtain a mixture;
   c) drying the mixture of (b) to obtain a dried mixture;
   d) optionally grinding the dried mixture of (c) to obtain a powder;
   e) coating the dried mixture of (c) or powder of (d); and
   f) mixing the coated dried mixture or powder of (e) with an excipient;
   wherein the protective compound is a cryoprotectant and/or lyoprotectant with a bulk density between 150 and 600 $kg/m^3$.

2. The method of claim 1, wherein the protective compound is a cryoprotectant and/or lyoprotectant with a bulk density between 150 and 225 $kg/m^3$.

3. The method of claim 1, wherein the protective compound is a cryoprotectant and/or lyoprotectant with a bulk density of about 180 $kg/m^3$.

4. The method of claim 1, wherein the method comprises step f) and further comprises the step of:
   g) adjusting the water activity (aw) of the excipient mixture of f) to about 0.35.

5. The method of claim 1, wherein said protective compound is a cryoprotectant and/or lyoprotectant comprising at least one ingredient selected from the group consisting of maltodextrin, oligofructose, pectin, xanthan gum, OSA starch and sodium ascorbate.

6. The method of claim 1, wherein said excipient is calcium carbonate.

* * * * *